(12) United States Patent
Perreault et al.

(10) Patent No.: US 7,148,044 B1
(45) Date of Patent: Dec. 12, 2006

(54) NUCLEIC ACID ENZYME FOR RNA CLEAVAGE

(75) Inventors: Jean-Pierre Perreault, Fleurimont (CA); Sirinart Ananvoranich, Westbury (CA); Daniel Lafontaine, Saint-Alexis de Montcalm (CA)

(73) Assignee: Universite de Sherbrooke, Quebec (CA)

( * ) Notice: Subject to any disclaimer, the term of this patent is extended or adjusted under 35 U.S.C. 154(b) by 945 days.

(21) Appl. No.: 09/699,667

(22) Filed: Oct. 30, 2000

Related U.S. Application Data

(63) Continuation of application No. PCT/CA99/00391, filed on Apr. 29, 1999.

(30) Foreign Application Priority Data

Apr. 29, 1998 (CA) .................................. 2230203

(51) Int. Cl.
 C12Q 1/68 (2006.01)
 C12P 19/34 (2006.01)
 C07H 21/00 (2006.01)
 C07H 21/02 (2006.01)
 C07H 21/04 (2006.01)

(52) U.S. Cl. .............. 435/91.31; 435/6; 435/91.1; 536/23.1; 536/24.3; 536/24.31; 536/24.32; 536/24.33; 536/24.5

(58) Field of Classification Search .............. 435/6, 435/91.1, 91.31, 455, 458, 320.1; 536/23.1, 536/24.5, 23.2, 24.3, 24.31, 24.32, 24.33
See application file for complete search history.

(56) References Cited

U.S. PATENT DOCUMENTS

| 5,225,337 A | 7/1993 | Robertson et al. |
| 5,625,047 A | 4/1997 | Been et al. |

FOREIGN PATENT DOCUMENTS

| WO | WO 92/07065 | 4/1992 |
| WO | WO 93/05157 | 3/1993 |
| WO | WO 93/14218 | 7/1993 |
| WO | WO 94/02595 | 2/1994 |

OTHER PUBLICATIONS

Ananvoranich, S. et al. J. Biol. Chem. vol. 273, No. 22, pp. 13, 182-13, 188 (1998).*
David V. Lazinski and John M. Taylor, (1995) Regulation of the hepatitis delta virus ribozymes: To cleave or not to cleave? RNA (1995), 1:225-233.
Andrea D. Branch and Hugh D. Robertson (1991) Efficient trans cleavage and a common structural motif for the ribozymes of the humans agent. Proc. Natl. Acad. Sci. USA. 88:10163-10167.
Anne T. Perrotta and Michael D. Been. (1991) A pseudoknot-like structure required for efficient self-cleavage of hepatitis delta virus RNA. Nature. 350: 434-436.
Adrian R. Ferré-D'Amaré, Kaihong Zhou and Jennifer A. Doudna. (1998) Crystal Structure of a hepatitis delta virus ribozyme. Nature. 395: 567-574.
Jean-Pierre Perrault, Taifeng Wu, Benoit Cousineau, Kevin K. Ogilvie and Robert Cedergren (1990) Mixed deoxyribo- and ribo-ligonucleotides with catalytic activity. Nature. 344: 565-567.
Michael D. Been and Gene S. Wickham (1997) Self-cleaving ribozymes of hepatitis delta virus RNA. Eur. J. Biochem. 247: 741-753.
Guylaine Roy, Sirinart Ananvoranich and Jean-Pierre Perreault, (1999) Delta ribozyme has the ability to cleave in trans an mRNA, Nucl. Acid Res. 27:942-948.
Sirinart Ananvoranich, Daniel A. Lafontaine and Jean-Pierre Perreaul (1999) Mutational analysis of the antigenomic trans-acting delta ribozyme: the alterations of the middle nucleotides located on the P1 stem Nucl. Acid Res. 27:1473-1479.
Wolfgang A. Picken, David B. Olsen, Fritz Benseler, Helle Aurup, Fritz Eckstein (1991) Kinetic Characterization of Ribonuclease-Resistant 2'-Modified Hammerhead Ribozymes, Science, 253: 314-317.

(Continued)

Primary Examiner—Jane Zara
(74) Attorney, Agent, or Firm—Jones Day

(57) ABSTRACT

A method is described for cleaving a nucleic acid substrate with a nucleic acid enzyme at a cleavage site comprising mixing the substrate with the enzyme, wherein the substrate includes a 7 nucleotide sequence with at least 6 nucleotides 3' to the cleavage site and at least 1 nucleotide 5' to the cleavage site and of formula:

5'-H'GNNHNN-3' wherein each N is a nucleotide which may be the same or different, H is a nucleotide selected from the group consisting of A, U, C, and T, and is the site of cleavage, and H' is a ribonucleotide selected from the group consisting of A, U, and C, wherein (i) the first nucleotide 3' to the cleavage site is capable of forming a wobble pair with the enzyme, (ii) the second, third, fifth, and sixth nucleotides 3' to the cleavage site are capable of forming conventional Watson-Crick base pairs with the enzyme, (iii) the fourth nucleotide 3' to the cleavage site is capable of forming a non-conventional Watson-Crick base pair with the enzyme, and (iv) the first nucleotide 5' to the cleavage site does not form a base pair with the enzyme; and the enzyme comprises a substrate binding portion which is capable of base pairing to the 6 nucleotides 3' to the cleavage site of the substrate and which binding portion comprises the sequence:

3'-UNNXNN-5' wherein each N is a nucleotide which may be the same or different, and X is a nucleotide selected from the group consisting of T, U, A, and G, whereby binding of the substrate to the enzyme effects cleavage of the substrate at the cleavage site.

11 Claims, 7 Drawing Sheets

OTHER PUBLICATIONS

Bharat M. Chowrira, Alfredo Berzal-Herranz, Charles F. Keller and John M. Burke (1993) Four Ribose 2'-Hydroxyl Groups Essential for Catalytic Function of the Hairpin Ribozyme, J. Biol. Chem. 268: 19458-19462.

Orna Elroy-Stein and Bernard Moss (1990) Cytoplasmic expression system based on constitutive synthesis of bacteriophage T7 RNA polymerase in mammalian cells Proc. Natl. Acad. Sci. USA 87: 6743-6747.

Xiang Gao and Leaf Huang (1993) Cytoplasmic expression of a reporter gene by co-delivery of T7 RNA polymerase and T7 promoter sequence with cationic liposomes Nucl. Acid Res. 21: 2867-2872.

Joshua O. Ojwang, Arnold Hampel, David J. Looney, Flossie Wong-Staal and Jay Rappaport, (1992) Inhibition of human immunodeficiency virus type 1 expression by a hairpin ribozyme Proc. Natl. Acad. Sci USA 89: 10802-10806.

Shinji Makino, Ming-Fu Chang, Chien-Kou Shieh, Toshio Kamahora, David M. Vannier, Sugantha Govindarajan, Michael M. C. Cai (1987) Molecular cloning and sequencing of a human hepatitis delta ($\delta$) virus RNA, Nature 329: 343-346.

Jean-Pierre Perreault and Sydney Altman (1992) Important 2'-hydroxyl Groups in Model Substrates for M1 RNA, the Catalytic RNA Subunit of RNase P from *Escherichia coli*, J. Mol. Biol. 226: 399-409.

Sirinart Ananvoranich and Jean-Pierre Perreault (1998) Substrate Specificity of $\delta$ Ribozyme Cleavage, J. Biol. Chem. 273: 13182-13188.

Thomas W. Traut, (1994) Physiological concentrations of purines and pyrimidines. Mol. Coll. Biochem. 140: 1-22.

Fabien Côté and Jean-Pierre Perreault (1997) Peach Latent Mosaic Viroid is locked by a 2',5'-Phosphodiester Bond Produced by *In Vitro* Self-ligation, J. Mol. Biol. 273: 533-543.

Daniel Lafontaine, Stéphane Mercure and Jean-Pierre Perreault (1997) Update of the viroid and viroid-like sequence database: addition of a hepatitis delta virus RNA section, Nucl. Acid. Res. 25: 123-125.

Mei Chao, Sen-Yung Hsieh and John Taylor (1990) Role of Two Forms of Hepatitis Delta Virus Antigen: Evidence for a Mechanism of Self-Limiting Genome Replication, J. Virol. 64: 5066-5069.

Stéphane Mercure, Daniel Lafontaine, Sirinart Ananvoranich and Jean-Pierre Perreault (1998) Kinetic Analysis of $\delta$ Ribozyme Cleavage, Biochemistry 37: 16975-16982.

Hamid Fauzi, Junji Kawakami, Fumiko Nishikawa and Satoshi Nishikaw (1997) Analysis of the cleavage reaction of a trans-acting human hepatitis delta virus ribozyme, Nucl. Acid Res. 25: 3124-3130.

M. Kashani-Sabet et al. (1992) Reversal of the Malignant Phenotype by an Anti-ras Ribozyme. Antisense Research and Development 2:3-15.

* cited by examiner

NUCLEIC ACID ENZYME FOR RNA CLEAVAGE

This application is a continuation of PCT/CA99/00391, filed Apr. 29, 1999, which claims priority to Canadian patent application 2,230,203, filed Apr. 29, 1998, both of which are incorporated herein in their entirety.

TECHNICAL FIELD

The invention relates to a novel ribozyme construction for the specific recognition and cleavage of RNA, and biotechnological as well as therapeutic uses thereof.

BACKGROUND ART

Though enzymatic activity has long been considered the exclusive domain of proteins, discoveries in molecular biology over the past couple of decades have led to the realization that ribonucleic acid (RNA) can also function as an enzyme. RNA enzymes are often referred to as ribozymes.

Ribozyme substrates are generally confined to RNA molecules, and enzymatic activities of ribozymes include the cleavage and/or ligation of RNA molecules. The cleavage activity may be intramolecular, known as cis-acting or intermolecular, known as trans-acting. There are at least five classes of ribozymes known, including Group I introns, Group II introns, hammerhead, hairpin, and delta ribozymes. The last three are derived from plant satellites and viroids.

Since 1982, several unexpected diseases caused by RNA-based pathogenic agents have emerged. These include the lethal Acquired Immune Deficiency Syndrome (AIDS) and delta hepatitis, a particularly virulent form of fulminant hepatitis caused by a viroid-like RNA agent. These blood-borne diseases are spread at the RNA level, manifest themselves in cells of patients, and are by now present within the bloodstream of millions of individuals. Conventional biotechnology, with its reliance on recombinant DNA methods and DNA-level intervention schemes, has been slow to provide valid approaches to combat these diseases.

Two forms of delta ribozymes, namely genomic and antigenomic, are derived, and referred to by, the polarity of the hepatitis delta virus (HDV) genome from which the ribozyme is generated. Like hammerhead and hairpin ribozymes, the delta ribozymes cleave a phosphodiester bond of their RNA substrates and give rise to reaction products containing a 5'-hydroxyl and a 2',3'-cyclic phosphate termini. They are metalloenzymes and a low concentration (<1 mM) of magnesium ($Mg^{2+}$) or calcium ($Ca^{2+}$) is required for delta ribozyme cleavage. Both genomic strand and antigenomic strand forms exhibit self-cleavage activity, and it has been suggested that they are involved in the process of viral replication (Lazinski, D. W., and Taylor, J. M. (1995) *RNA* 1, 225–233).

Delta ribozymes derived from the genome of HDV are of interest in the development of a gene regulation system in which the designed ribozymes would down-regulate the expression of a target gene. The facts that delta ribozymes are derived from HDV and that this pathogen naturally replicates in animal systems, suggest that this catalytic RNA could be used to control gene expression in human cells. Like other ribozymes, the designed ribozyme should specifically cleave its target substrates while leaving other cellular RNA molecules intact.

Trans-acting ribozymes carry out intermolecular cleavage activity. Some trans-acting delta ribozymes have been developed by removing a single-stranded junction which connects the catalytic portion to the substrate portion in cis-acting delta ribozymes. This results in two separate molecules, one possessing the substrate sequence and the other the catalytic property (Been, M. D. and Wichhan, G. S. (1997) *Eur. J. Biochem.*, 247, 741–753). Interactions between such delta ribozymes and the substrate occur through the formation of a helix, referred as the P1 stem. However, the example of the trans-acting ribozyme disclosed by Been et al. (supra) was not useful for cleaving long substrate molecules, such as those having therapeutic applications.

In U.S. Pat. No. 5,225,337, issued on Jul. 6, 1993 in the names of Hugh D. Robertson et al., there are disclosed ribozymes derived from a specific domain present in the HDV RNA for specifically cleaving targeted RNA sequences and uses thereof for the treatment of disease conditions which involve RNA expression, such as AIDS. These ribozymes consist of at least 18 consecutive nucleotides from the conserved region of HDV isolates between residues 611 and 771 on the genomic strand and between residues 845 and 980 on the complementary antigenomic strand. These ribozymes are proposed to fold into an axehead model secondary structure (Branch, A. D., and Robertson, H. D. (1991) *Proc. Natl. Acad. Sci. USA* 88, 10163–10167). The ribozymes developed according to this model structure require the substrate to be bound to the ribozyme through the formation of two helices, one located on either side of the cleavage site. Further, such ribozymes apparently require a 12–15 nucleotide recognition sequence in the substrate in order to exhibit the desired activity. Such a long recognition sequence is not practical in the development of therapeutic or diagnostic applications.

In U.S. Pat. No. 5,625,047, issued on Apr. 29, 1997 in the names of Michael D. Been et al., there are disclosed enzymatic RNA molecules proposed to fold into a pseudoknot model secondary structure (discussed below). The method disclosed for the development of efficient ribozymes requires a short recognition sequence of only 7 to 8 nucleotides in the substrate, a preference for a guanosine base immediately 3' to the cleavage site, a preference for U, C or A immediately 5' to the cleavage site, and the availability of a 2'-hydroxyl group for cleavage to occur. Thus, the specificity of recognition of these ribozymes is limited to 6 or 7 base pairing nucleotides with the substrate and a preference of the first nucleotide located 5' to the cleavage site. Neither tertiary interaction(s) between the base paired nucleotides and another region of the ribozyme, nor single-stranded nucleotides are involved to define the specificity of recognition of these ribozymes. Because the recognition features are limited, these ribozymes have a limited specificity, and thus, are not practical for further clinical or biotechnical applications.

A pseudoknot-like structure for delta ribozymes has been proposed by Perrotta and Been (Perrotta, A. T., and Been, M. D. (1991) *Nature* 350, 434–436). This model structure consists of two stems (P1 and P2), two stem-loops (P3 and P4) and three single-stranded regions (J1/2, J1/4 and J4/2). An additional stem, named P1.1, has been formed by two GC base pairs between nucleotides from the J1/4 junction and the P3 loop (Ferré-D'Amaré, A. R., Zhou, K. and Doudna, J. A. (1998) *Nature*, 350, 434–436).

It would be highly desirable to be provided with a novel delta ribozyme for the cleavage of both small and large RNA substrates for which the specificity of recognition is well defined. Such specificity would yield optimal conditions for further therapeutical and biotechnological developments of delta ribozymes.

SUMMARY OF THE INVENTION

One aim of the present invention is to provide a novel delta ribozyme for the cleavage of RNA substrates for which the specificity is defined by a domain composed of at least 7 nucleotides. It is also an aim to provide a method for the development of such ribozymes.

In one aspect, the invention provides a method for cleaving a nucleic acid substrate with a nucleic acid enzyme at a cleavage site comprising mixing the substrate with the enzyme, wherein the substrate includes a 7 nucleotide sequence with at least 6 nucleotides 3' to the cleavage site and at least 1 nucleotide 5' to the cleavage site of formula:

5'-H'GNNHNN-3' wherein each
  N is a nucleotide which may be the same or different,
  H is a nucleotide selected from the group consisting of A, U, C, and T, and
    is the site of cleavage, and
  H' is a ribonucleotide selected from the group consisting of A, U, and C, wherein
  (i) the first nucleotide 3' to the cleavage site is capable of forming a wobble pair with the enzyme,
  (ii) the second, third, fifth, and sixth nucleotides 3' to the cleavage site are capable of forming conventional Watson-Crick base pairs with the enzyme,
  (iii) the fourth nucleotide 3' to the cleavage site is capable of forming a triplet with the enzyme comprising a non-conventional Watson-Crick base pair and a conventional Watson-Crick base pair, and
  (iv) the ribonucleotide directly 5' to the cleavage site does not form a base pair with the enzyme; and the enzyme comprises a substrate binding portion which is capable of base pairing to the 6 nucleotides 3' to the cleavage site of the substrate and which binding portion comprises the sequence:

3'-UNNXNN-5' wherein each
  N is a nucleotide which may be the same or different, and
  X is a nucleotide selected from the group consisting of T, U, A, and G, whereby binding of the substrate to the enzyme effects cleavage of the substrate at the cleavage site.

In another aspect, the invention provides a nucleic acid enzyme capable of recognizing and cleaving a nucleic acid substrate at a cleavage site comprising a substrate binding portion which is capable of base pairing to the 6 nucleotides 3' to the cleavage site of the substrate and which binding portion comprises the sequence:

3'-UNNXNN-5' wherein each
  N is a nucleotide which may be the same or different, and
  X is a nucleotide selected from the group consisting of T, U, A, G, and the substrate includes a 7 nucleotide sequence with at least 6 nucleotides 3' to the cleavage site and at least 1 nucleotide 5' to the cleavage site of formula:

5'-H'GNNHNN-3' wherein each
  N is a nucleotide which may be the same or different,
  H is a nucleotide selected from the group consisting of A, U, C, and T,
    is the site of cleavage, and
  H' is a ribonucleotide selected from the group consisting of A, U, and C, wherein
  (i) the first nucleotide 3' to the cleavage site is capable of forming a wobble pair with the enzyme,
  (ii) the second, third, fifth, and sixth nucleotides 3' to the cleavage site are capable of forming conventional Watson-Crick base pairs with the enzyme,
  (iii) the fourth nucleotide 3' to the cleavage site is capable of forming a triplet with the enzyme comprising a non-conventional Watson-Crick base pair and a conventional Watson-Crick base pair, and
  (iv) the first ribonucleotide directly 5' to the cleavage site does not form a base pair with the enzyme.

Figure 1A:
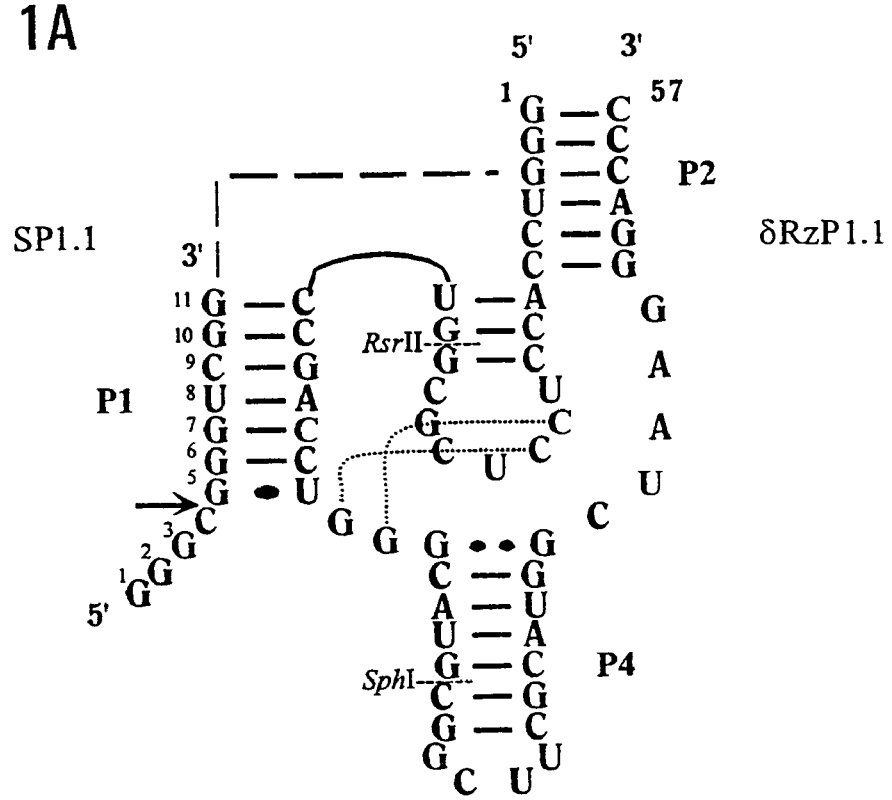
FIG. 1 illustrates the secondary structure and nucleotide sequences of two trans-acting antigenomic delta ribozymes of the invention and complementary substrates; panel A is the secondary structure of the complex formed between δRzP1.1 and a substrate Sp1.1; panel B is the P1 region of the complex formed between δRzP1.2 and a substrate Sp1.2; the rest of the structure is identical to δRzP1.1 as in panel A.

the recognition site on the mRNA is located on the pres-S2 and S mRNA (2.1 kb, as shown in Panel A); the arrow indicates the cleavage site.

DESCRIPTION OF THE PREFERRED EMBODIMENTS OF THE INVENTION

The subject invention provides for a method of designing selective nucleic acid enzymes, such that a nucleic acid substrate is cleaved at a specified cleavage site by the nucleic acid enzyme. This method includes the selection of certain substrate sequences and, within the enzymes, certain substrate binding sequences, such that efficient cleavage at a specified site in the nucleic acid substrate can take place. The subject invention also provides for nucleic acid enzymes designed using such method.

For the purpose of the present invention the following abbreviations are defined: "A" is a nucleotide comprising adenine including both the ribo- and deoxyribo-forms; "G" is a nucleotide comprising guanine including both the ribo- and deoxyribo-forms; "C" is a nucleotide comprising cytidine including both the ribo- and deoxyribo-forms; "U" is a nucleotide comprising uracil; "T" is a nucleotide comprising thymine; "R" is a nucleotide comprising purine, which purine is selected from the group consisting of A and G; and "Y" is a nucleotide comprising pyrimidine, which pyrimidine is selected from the group consisting of U, C, and T.

Selection of Substrate Sequence

Substrate nucleic acid includes any nucleic acid sequence which can act as a substrate for a nucleic acid enzyme of the invention. As such it includes ribonucleotides, deoxyribonucleotides, or mixtures of both. Nucleotides may also include synthetic or modified nucleotides.

The nucleic acid enzymes of the invention can be used to target a large number of nucleic acid substrates so long as certain conditions of the recognition mechanism are met. The nucleic acid substrate must include a 7 nucleotide sequence with at least 6 nucleotides 3' to the cleavage site and at least 1 nucleotide 5' to the cleavage site of formula:

5'-H'GNNHNN-3' wherein each

N is a nucleotide which may be the same or different,

H is a nucleotide selected from the group consisting of A, U, C, and T, and is the site of cleavage, and H' is a ribonucleotide selected from the group consisting of A, U, and C.

The first nucleotide 3' to the cleavage site is capable of forming a wobble pair with the enzyme. The wobble base pair (G-U) at the cleavage site is required to maintain a high level of cleavage. Conventional Watson-Crick base pairs such as A-U and G-C, as well as mismatches at this position decrease the cleavage activity.

The second, third, fifth, and sixth nucleotides 3' to the cleavage site are capable of forming conventional Watson-Crick base pairs with the enzyme.

The fourth nucleotide 3' to the cleavage site is capable of forming a conventional Watson-Crick base pair with the substrate binding region of the enzyme. Additionally, such base pair interacts with a nucleotide elsewhere in the ribozyme (i.e. the nucleic acid enzyme) to form a triplet by means of a non-conventional Watson-Crick base pair. Non-conventional Watson-Crick base pairs include Hoogsteen pairs and reversed-Hoogsteen pairs. The position requires an A, U, or C.

The ribonucleotide directly 5' to the cleavage site does not form a base pair with the ribozyme.

Preferably, the substrate molecule does not contain two consecutive pyrimidine nucleotides directly 5' to the cleavage site.

In another preferred aspect, the substrate comprises the sequence 5'-H' GNNHNNN-3', more preferably the sequence 5'-NNRH' GNNHNNN-3', wherein R is G or A.

In one embodiment, the substrate preferably comprises the sequence 5'-RRRH' GNNHNNN-3'. More preferably, such sequence is selected from the group consisting of 5'-GGGC GNNUNNN-3', 5'-GGGC GNNCNNN-3', 5'-GGGU GNNUNNN-3', 5'-GGGU GNNCNNNN-3', and 5'-AAAC GNNUNNN-3'.

In another embodiment, the substrate preferably comprises the sequence 5'-YHRH' GNNHNNN-3', wherein Y is C, U, or T. It is preferred that the four nucleotides directly 5' to the cleavage site are chosen such that Y is C or U, preferably C; H is one of U, C, or A, preferably U or C, more preferably U; R is preferably A; and H is A, C, or U, preferably A or C, more preferably A.

It is preferable that the four nucleotides directly 5' to the cleavage site do not form a hairpin structure.

Selection of Ribozyme Sequence

By ribozymes, it is meant a nucleic acid enzyme, in other words any nucleic acid sequence having enzymatic activity, i.e. the ability to catalyze a reaction. As such it includes nucleic acid sequences made up of ribonucleotides, deoxyribonucleotides, or mixtures of both. Nucleotides may also include synthetic or modified nucleotides.

The selection of the sequence of the substrate binding region of the ribozyme, should be done such that the binding region comprises the sequence 3'-UNNXNN-5', wherein each N is a nucleotide which may be the same or different, and X is a nucleotide selected from the group consisting of T, U, A, and G.

The invention preferably provides for a nucleic acid enzyme with a secondary structure which comprises three or more distinct double-stranded regions, or stem-regions. This includes regions of base-pairing which may or may not be capped by a single-stranded loop, to form a stem-loop region. Preferably, the nucleic acid ribozyme includes two or more distinct single-stranded regions, one of which includes a substrate binding region which will base pair to the substrate. More preferably there are two single stranded regions.

The invention preferably contemplates the use of nucleic acid enzymes derived from hepatitis delta virus, known as delta ribozymes.

Generation of Ribozyme and Substrate

Trans-acting delta ribozymes of the invention were generated based on the pseudoknot-like structure proposed by Perrotta and Been, by removing the single-stranded region (region J1/2) located at the junction between the P1 and P2 stems. In addition, the P2 stem was elongated, by introducing, for instance, three G-C base pairs, and by shortening the P4 stem.

Figure 1B:
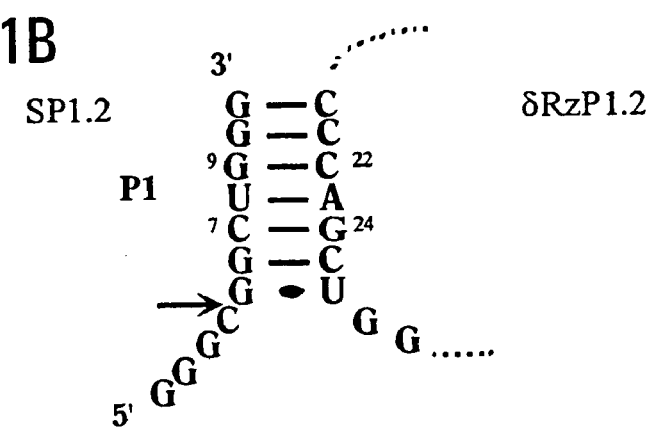

FIG. 1 illustrates an example of two ribozymes, δRzP1.1 and δRzP1.2, in accordance with one aspect of the invention. The base paired regions of the pseudoknot-like structure are numbered according to Perrotta and Been (Perrotta, A. T., and Been, M. D. (1991) *Nature* 350, 434–436). The dashed line represents the J1/2 single-stranded region joining the substrate and ribozyme molecules present in the cis-form. This single-stranded area was eliminated to produce a trans-acting ribozyme of the invention. The arrow indicates the cleavage site. The homopurine basepair at the top of the P4 stem is represented by two dots (G• •G), while the wobble base pair is represented by a single dot (G•U). The two small dotted lines illustrate the P1.1 stem formed by two GC base pairs.

Figure 2:
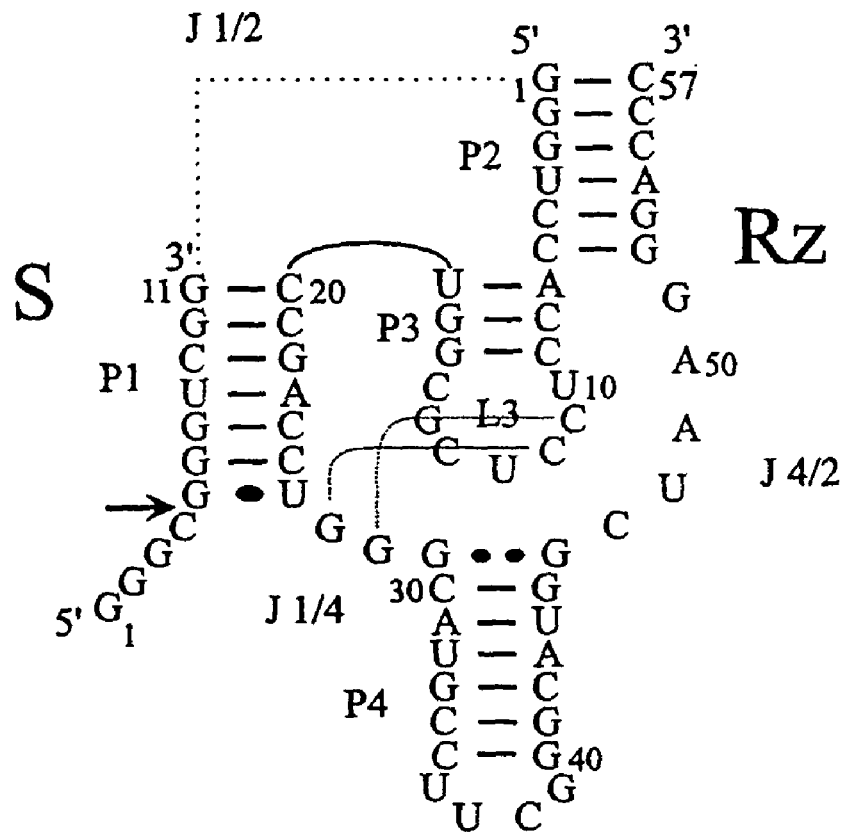
FIG. 2 illustrates the secondary structure of a ribozyme in accordance with the invention, with an ultrastable L4 loop; in the inset is the sequence of a 14-nucleotide long substrate.
Figure 2:
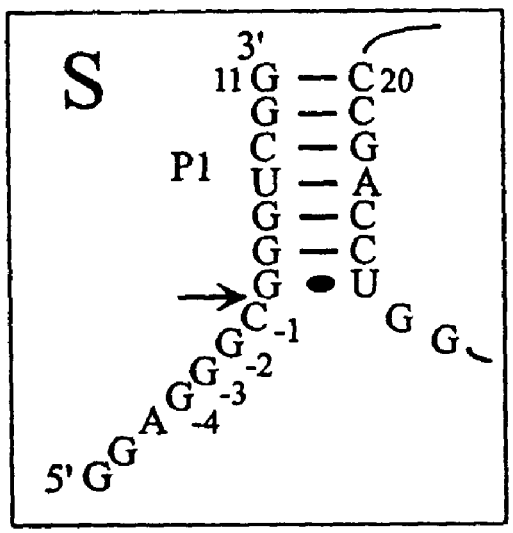
Figure 3:
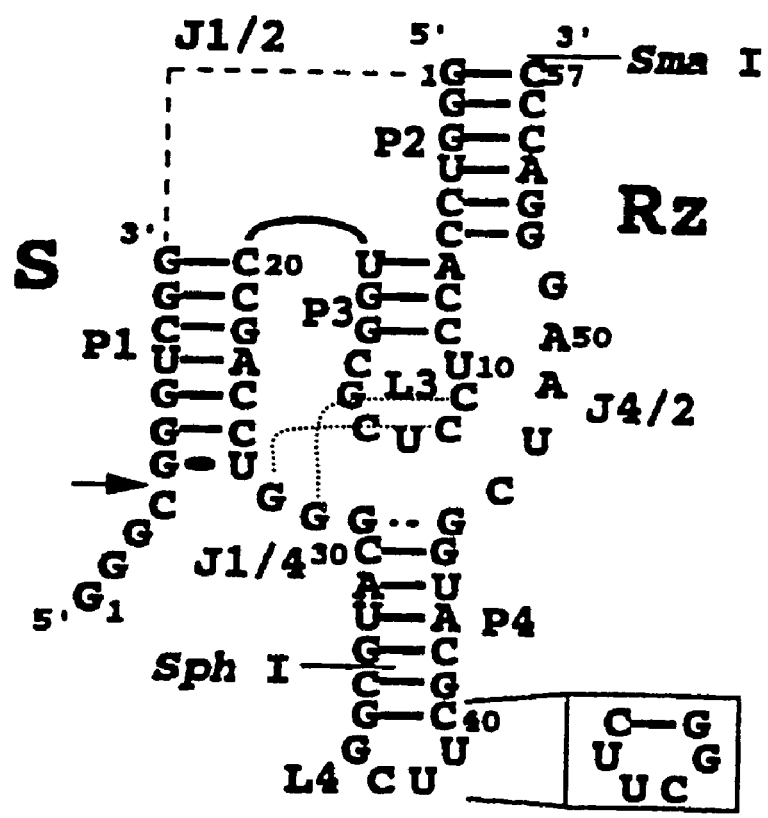
FIG. 3 illustrates the secondary structure of a ribozyme in accordance with the invention; the inset shows the ultrastable L4 loop.

In another aspect, the invention provides for a ribozyme with an elongated P2 stem and shortened P4 stem, which further comprises a modification of the L4 loop. FIGS. 2 and 3 show ribozymes in accordance with this embodiment. S and Rz represent substrate and ribozyme respectively.

Figure 4:
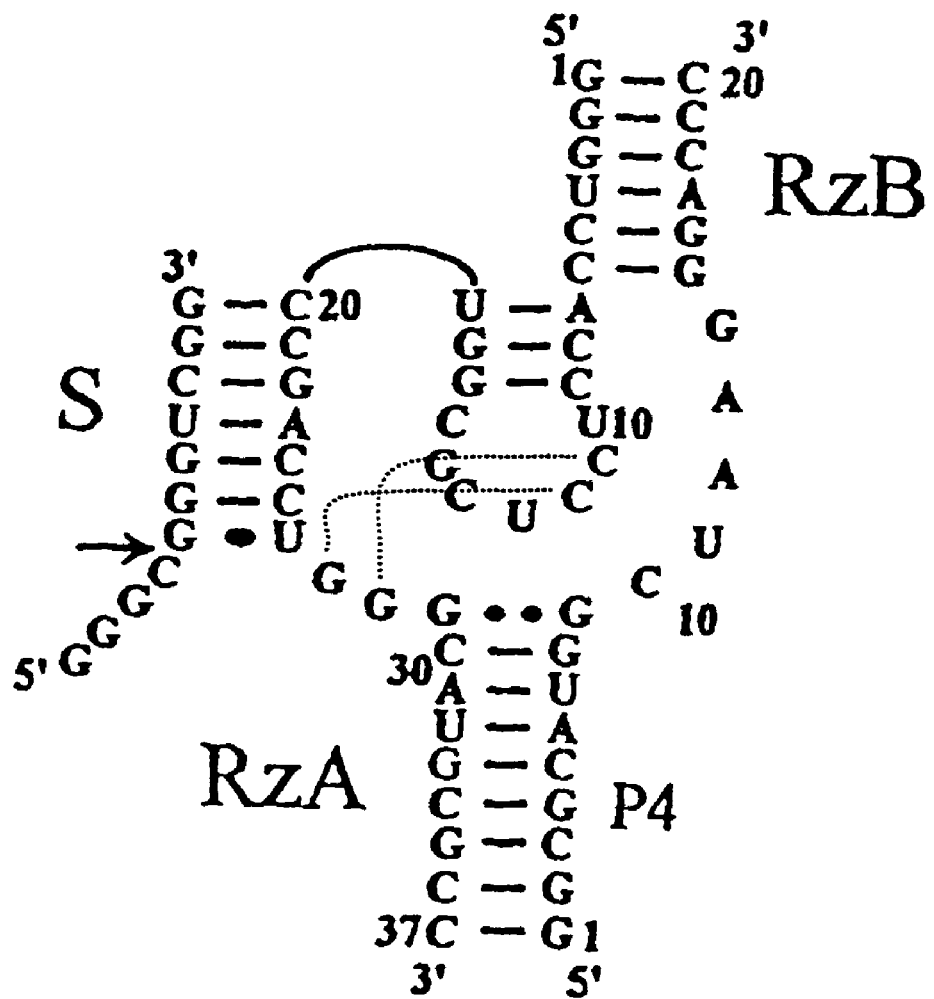
FIG. 4 shows a two-dimensional representation of a catalytic trimolecular complex (RzA:RzB:S) of the invention.

In one aspect, the invention provides for a bimolecular ribozyme. This may be achieved by removal of the L4 loop. FIG. 4 shows a ribozyme in accordance with this embodiment.

Applications

Ribozyme activity can be optimized by chemically synthesizing ribozymes with modifications that prevent their degradation by serum ribonucleases (see e.g., Eckstein et al., International Publication No. WO 92/07065; Perreault et al., Nature 1990, 344:565; Pieken et al., Science 1991, 253:314; and Chowrira et al., 1993 J. Biol. Chem. 268, 19458, which describe various chemical modifications that can be made to the sugar moieties of enzymatic RNA molecules, all of which publications are incorporated by reference herein), modifications which enhance their efficacy in cells, and removal of helix-containing bases to shorten RNA synthesis times and reduce chemical requirements.

In one aspect, the invention provides a substrate molecule which is a target RNA, such as a viral RNA, or an RNA crucial to the life cycle of a pathogen, or an RNA manifested as a result of an inherited disease, based on the substrate specificity described herein.

Ribozymes are added directly, or can be complexed with cationic lipids, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Sullivan, et al., (WO 94/02595, incorporated by reference herein), describes general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan, et al., ("Method and Reagent for Treatment of Arthritic Conditions" U.S. Ser. No. 08/152,487, filed Nov. 12, 1993, and incorporated by reference herein).

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein, O. and Moss, B., 1990, Proc. Natl. Acad. Sci. USA, 87, 6743–7; Gao, X. and Huang;, L., 1993, Nucleic Acids Res., 21, 2867–72; hereby incorporated by reference). Several investigators have demonstrated that ribozymes expressed from such promoters can function in mammalian cells (e.g. Kashani-Sabet, M., et al., 1992, Antisense Res. Dev., 2, 3–15; Ojwang, J. O., et al., 1992, Proc. Natl. Acad. Sci. USA, 89, 10802–6; hereby incorporated by reference). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, Semliki forest virus, hepatitis delta virus, and sindbis virus vectors).

Thus, ribozymes of the present invention that cleave target mRNA and thereby inhibit and/or reduce target activity have many potential therapeutic uses, and there are reasonable modes of delivering the ribozymes in a number of the possible indications.

By "inhibit" is meant that the activity or level of target RNA is reduced below that observed in the absence of the ribozyme, and preferably is below that level observed in the presence of an inactive RNA molecule able to bind to the same site on the RNA, but unable to cleave that RNA.

By "vectors" is meant any nucleic acid and/or viral-based construct used to deliver a desired nucleic acid.

EXAMPLES

Example 1

Preparation of Ribozymes, Substrates, and Plasmids.

Construction of plasmids carrying ribozymes of the invention. The antigenomic ribozyme sequence of the hepatitis delta virus described by Makino et al (Makino, S. et al. (1987) *Nature* 329, 343–346, hereby incorporated by reference) was used as the basis for generating trans-acting delta ribozymes of the invention. Briefly, the construction was performed as follows. Two pairs of complementary and overlapping oligonucleotides, representing the entire length of the ribozyme (57 nt), were synthesized and subjected to an annealing process prior to cloning into pUC19. The annealed oligonucleotides were ligated to HindIII and SmaI co-digested pUC19 to give rise to a plasmid harboring the delta ribozyme (referred to as pδRzP1.1). The minigene was designed so as to have unique SphI and SmaI restriction sites. The sequence of the T7 RNA promoter was included at the 5' end of the ribozyme so as to permit in vitro transcription. Variations based on this "wild type" ribozyme are constructed by replacing the SphI-SmaI fragment of pδRzP1.1 by an oligonucleotide duplex containing the desired sequence. The sequences of engineered ribozymes were confirmed by DNA sequencing. Plasmids containing wild type and mutant ribozymes were then prepared using Qiagen tip-100 (Qiagen Inc.), digested with SmaI, purified by phenol and chloroform extraction and precipitated for further use as templates for in vitro transcription reactions.

Synthesis of Ribozymes and Substrates. Ribozyme: In vitro transcription reactions contained 5 μg linearized recombinant plasmid DNA as template, 27 units RNAGuard (RNase inhibitor (Pharmacia), 4 mM of each rNTP (Pharmacia), 80 mM HEPES-KOH pH 7.5, 24 mM $MgCl_2$, 2 mM spermidine, 40 mM DTT, 0.01 unit Pyrophosphatase (Boehringer Mannheim) and 25 μg purified T7 RNA polymerase in a final volume of 50 μL, and were incubated at 37° C. for 4 hr. Substrates: Deoxyoligonucleotides (500 pmoles) containing the substrate and the T7 promoter sequence were denatured by heating at 95° C. for 5 min in a 20 μL mixture containing 10 mM Tris-HCl pH 7.5, 10 mM $MgCl_2$, 50 mM $KCl_2$, and allowed to cool slowly to 37° C. The in vitro transcription reactions were carried out using the resulting partial duplex formed as template under the same conditions as described for the production of the ribozyme.

After incubation, the reaction mixtures were fractionated by denaturing 20% polyacrylamide gel electro-phoresis (PAGE, 19:1 ratio of acrylamide to bisacrylamide) containing 45 mM Tris-borate pH 7.5, 7 M urea and 1 mM EDTA. The reaction products were visualized by UV shadowing. The bands corresponding to the correct sizes of either ribozymes or substrates were cut out, and the transcripts eluted overnight at 4° C. in a solution containing 0.1% SDS and 0.5 M ammonium acetate. The transcripts were then precipitated by the addition of 0.1 vol 3 M sodium acetate pH 5.2 and 2.2 vol ethanol. Transcript yield was determined by spectrophotometry.

Synthesis and Purification of RNA and RNA/DNA Mixed Polymer: RNA and RNA-DNA mixed polymers were sythesized on an automated oligonucleotide synthesizer, and deprotected according to previously described procedures (Perreault, J. P., and Altman, S. (1992) J. Mol. Biol. 226, 339–409 hereby incorporated by reference). These polymers were purified by 20% PAGE. Major bands were excised and eluted as described above.

End-labelling of RNA with [γ-32P]ATP. Purified transcripts (10 pmoles) were dephosphorylated in a 20 μL reaction mixture containing 200 mM Tris-HCl pH 8.0, 10 units RNA guard, and 0.2 unit calf intestine alkaline phosphatase (Pharmacia). The mixture was incubated at 37° C. for 30 min, and then extracted twice with a same volume of phenol:chloroform (1:1). Dephosphorylated transcripts (1 pmole) were end-labelled in a mixture containing 1.6 pmole [γ-32P]ATP, 10 mM Tris-HCl pH 7.5, 10 mM $MgCl_2$, 50 mM KCl and 3 units T4 polynucleotide kinase (Pharmacia) at 37° C. for 30 min. Excess [γ-32P]ATP was removed by applying the reaction mixture onto a spin column packed with a G-50 Sephadex gel matrix (Pharmacia). The concentration of labelled transcripts was adjusted to 0.01 pmol per mL by the addition of water.

Example 2

Kinetics

Cleavage reactions. To initiate a cleavage reaction, various concentrations of ribozymes were mixed with trace amounts of substrate (final concentration <1 nM) in a 18 mL reaction mixture containing 50 mM Tris-HCl pH 7.5, and subjected to denaturation by heating at 95° C. for 2 min. The mixtures were quickly placed on ice for 2 min and equilibrated to 37° C. for 5 min prior to the initiation of the reaction. Unless stated otherwise, cleavage was initiated by the addition of $MgCl_2$ to 10 mM final concentration. The cleavage reactions were incubated at 37° C., and followed for 3.5 hours or until the endpoint of cleavage was reached. The reaction mixtures were periodically sampled (2–3 μL), and these samples were quenched by the addition of 5 μL stop solution containing 95% formamide, 10 mM EDTA, 0.05% bromophenol blue and 0.05% xylene cyanol. The resulting samples were analyzed by a 20% PAGE as described above. Both the substrate and the reaction product bands were detected using a Molecular Dynamic radioanalytic scanner after exposition of the gels to a phosphoimaging screen.

Kinetic analysis. Measurement of pseudo-first-order rate constant ($k_{cat}$, $K_M$ and $k_{cat}/K_M$) were performed under single turnover conditions. Briefly, trace amounts of end-labelled substrate (<1 nM) were cleaved by various ribozyme concentrations (5 to 500 nM). The fraction cleaved was determined, and the rate of cleavage ($k_{obs}$) obtained from fitting the data to the equation $At=A\infty(1-e^{-kt})$ where At is the percentage of cleavage at time t, $A\infty$ is the maximum percent cleavage (or the end point of cleavage), and k is the rate constant ($k_{obs}$). Each rate constant was calculated from at least two measurements. The values of $k_{obs}$ obtained were then plotted as a function of ribozyme concentrations for determination of the other kinetic parameters: $k_{cat}$, $K_M$ and $k_{cat}/K_M$. Values obtained from independent experiments varied less than 15%. The requirement for $Mg^{2+}$ by both ribozymes was studied by incubating the reaction mixtures with various concentrations of $MgCl_2$ (1 to 500 mM) in the presence of an excess of ribozyme (500 nM) over substrate (<1 nM). The concentrations of $Mg^{2+}$ at the half maximal velocity were determined for both ribozymes. Determination of equilibrium dissociation constants ($K_d$). For mismatched substrates which could not be cleaved by the ribozyme, the equilibrium dissociation constants were determined. Eleven different ribozyme concentrations, ranging from 5 to 600 nM, were individually mixed with trace amounts of end-labelled substrates (<1 nM) in a 9 μL solution containing 50 mM Tris-HCl pH 7.5, heated at 95° C. for 2 min and cooled to 37° C. for 5 min prior to the addition of $MgCl_2$ to a final concentration of 10 mM, in a manner similar to that of a regular cleavage reaction. The samples were incubated at 37° C. for 1.5 h, at which 2 μL of sample loading solution (50% glycerol, 0.025% of each bromophenol blue and xylene cyanol) was added, and the resulting mixtures were electrophoresed through a nondenaturing polyacrylamide gel (20% acrylamide with a 19:1 ratio of acrylamide to bisacrylamide, 45 mM Tris-borate buffer pH 7.5 and 10 mM $MgCl_2$). Polyacrylamide gels were pre-run at 20 W for 1 h prior to sample loading, and the migration was carried out at 15 W for 4.5 h at room temperature. Quantification of bound and free substrates was performed following an exposure of the gels to a phosphoimaging screen as described earlier.

Example 3

Determination of Ribozyme and Substrate Sequence Specificity

A number of ribozymes and substrates were made, some of which are in accordance with the invention and others of which are comparative examples. Analysis of the kinetic parameters of cleavage reactions carried out using said ribozymes and substrates led to the characterizations of the method for selecting the ribozyme and substrate sequences. A summary of the kinetic data is given below.

i) Selection of a Substrate Comprising the Sequence 5'-H' GNNHNN-3' or 5' RRRH' GNNHNNN-3' and a Ribozyme Comprising the Sequence 3'-UNNXNN-5'.

Two forms of trans-acting delta ribozymes, δRzP1.1 and δRzP1.2 were used with their corresponding substrates (11 nt) SP1.1 and SP1.2 for the kinetic studies (see Table 1). The sequences of δRzP1.1, δRzP1.2, SP1.1 and SP2.2 are given in FIG. 1. δRzP1.2 differs from δRzP1.1 in that δRzP1.2 has two nucleotides, at positions 22 and 24 of δRzP1.1, interchanged (5'-CC<u>C</u>A<u>G</u>CU-3').

TABLE 1

Kinetic parameters of wild type ribozyme (δRzP1.1) and mutant ribozyme (δRzP1.2). Under single turnover conditions, trace amounts of end-labelled substrate (<1 nM) were cleaved by various concentrations of ribozyme (5 to 600 nM). Reactions carried out under these conditions displayed monophasic kinetics. The values were calculated from at least two independent experiments, and standard variations were less than 15%.

| Kinetic parameters | δRzP.1 | δRzP.2 |
|---|---|---|
| $k_{cat}$ (min$^{-1}$) | 0.34 ± 0.02 | 0.13 ± 0.01 |
| $K_M'$ (nM) | 17.9 ± 5.6 | 16.7 ± 6.4 |
| $k_{cat}/K_M'$ (min$^{-1}$·M$^{-1}$) | 1.89 × 10$^7$ | 0.81 × 10$^7$ |
| $K_{Mg}$ (mM) | 2.2 ± 1.0 | 2.1 ± 0.8 |

In order to compare the specificity of the delta ribozyme with various substrates, δRzP1.1 was used under single turnover conditions as described above. The cleavage reactions were performed with a trace amount of each substrate (<1 nM) and 500 nM δRzP1.1. Under these conditions, the observed rates reflect the rates of cleavage without interference from either product dissociation or inhibition. For each substrate both the observed cleavage rate constants ($k_{obs}$) and the extent of cleavage were calculated and compared to those of the wild type substrate, as shown in Table 2.

TABLE 2

Cleavage activity of shorter or mismatched substrates as compared to the wild type substrate (SP.1). Bold letters represent the nucleotides of wild type substrate recognized by δRzP1.1. The numbers in subscript indicate the nucleotides of wild type substrate which were individually altered to generate shorter or mismatched substrates.

| Substrates | Sequence | $k_{obs}$[a] (min$^{-1}$) | Extent of cleavage[c] (%) | $k_{rel}$[d] | ΔΔG[I,e] (kcal/mol) |
|---|---|---|---|---|---|
| Wild type substrate (S11-mer) | GGGCG$_5$G$_6$G$_7$U$_8$C$_9$G$_{10}$G$_{11}$ | 0.34 ± 0.02 | | 1 | — |
| S10-mer | GGGCGGGUCG | 0.022 ± 0.01 | 28.8 ± 4.3 | 0.063 | −1.69 |
| S9-mer | GGGCGGGUC | na[b] | na[b] | — | — |
| S8-mer | GGGCGGGU | na[b] | na[b] | — | — |
| SG5A | GGGCAGGUCGG | 0.009 ± 0.002 | 20.0 ± 2.4 | 0.026 | −2.25 |
| SG5C | GGGCCGGUCGG | 0.047 ± 0.017 | 1.7 ± 0.2 | 0.138 | −1.22 |
| SG6A | GGGCGAGUCGG | 0.026 ± 0.006 | 5.8 ± 0.5 | 0.076 | −1.59 |
| SG6U | GGGCGUGUCGG | 0.071 ± 0.026 | 3.7 ± 0.3 | 0.209 | −0.96 |
| SG7A | GGGCGGAUCGG | na[b] | na[b] | — | — |
| SG7U | GGGCGGUUCGG | na[b] | na[b] | — | — |
| SU8C | GGGCGGGCCGG | na[b] | na[b] | — | — |
| SU8G | GGGCGGGGCGG | na[b] | na[b] | — | — |
| SC9A | GGGCGGGUAGG | 0.016 ± 0.007 | 8.2 ± 3.0 | 0.047 | −1.88 |
| SC9U | GGGCGGGUUGG | 0.031 ± 0.005 | 21.2 ± 1.0 | 0.091 | −1.48 |
| SG10U | GGGCGGGUCUG | 0.016 ± 0.002 | 8.4 ± 0.5 | 0.047 | −1.88 |
| SG11U | GGGCGGGUCGU | 0.011 ± 0.001 | 32.1 ± 2.5 | 0.032 | −2.12 |

[a] $k_{obs}$ is the observed rate of cleavage calculated from at least two measurements.
[b] na represents no detectable cleavage activity after 3.5 hours incubation.
[c] Cleavage extent (%) is obtained by fitting the data to the equation $A_t = A\infty (1-e^{-kt})$, where $A_t$ is the percentage of cleavage at time t, A∞ is the maximum percentage of the cleavage, and k is the rate constant.
[d] $k_{rel}$ is the relative rate constant as compared to that of wild type substrate.
[e] ΔΔG$^I$, the apparent free energy of transition-state stabilization, was calculated using the equation ΔΔG$^I$ = RTln$k_{rel}$, where T = 310.15 K (37° C.) and R = 1.987 cal·K$^{-1}$mol$^{-1}$.

Further trans-acting delta ribozyme variants were produced using plasmid pδRzP1.1. The variants have either A23 or C24 mutated to one of the other three possible bases. The six resulting delta ribozyme variants are named for the altered nucleotide (δRzP1-A23C, -A23G, -A23U, -C24A, -C24G, and -C24U; Table 3). Complementary or compensatory substrates (Table 3) were generated in which either position 7 or 8 of the wild type substrate (SP1.1) was altered in order to restore the Watson-Crick base pair formation of the P1 stem between the substrates and the ribozyme variants.

TABLE 3

| Transcripts | Sequence | |
|---|---|---|
| Substrates | | |
| SP1.1 | $_1$GGGCGGGUCGG$_{11}$ | (SEQ ID: 9) |
| SG7A | GGGCGGAUCGG | (SEQ ID: 15) |
| SG7C | GGGCGGCUCGG | (SEQ ID: 23) |
| SG7U | GGGCGGUUCGG | (SEQ ID: 16) |
| SU8A | GGGCGGGACGG | (SEQ ID: 24) |
| SU8C | GGGCGGGCCGG | (SEQ ID: 17) |
| SU8G | GGGCGGGGCGG | (SEQ ID: 18) |
| SU8G-9mers | $_1$GCGGGGCGG$_9$ | |
| Ribozymes | | |
| δRzP1.1 | $_{20}$CCGACCU$_{26}$ | |
| δRzP-A23C | CCGCCCU | |
| δRzP1-A23G | CCGGCCU | |
| δRzP1-A23U | CCGUCCU | |
| δRzP1-C24A | CCGAACU | |
| δRzP1-C24G | CCGAGCU | |
| δRzP1-C24U | CCGAUCU | |

Figure 5A:
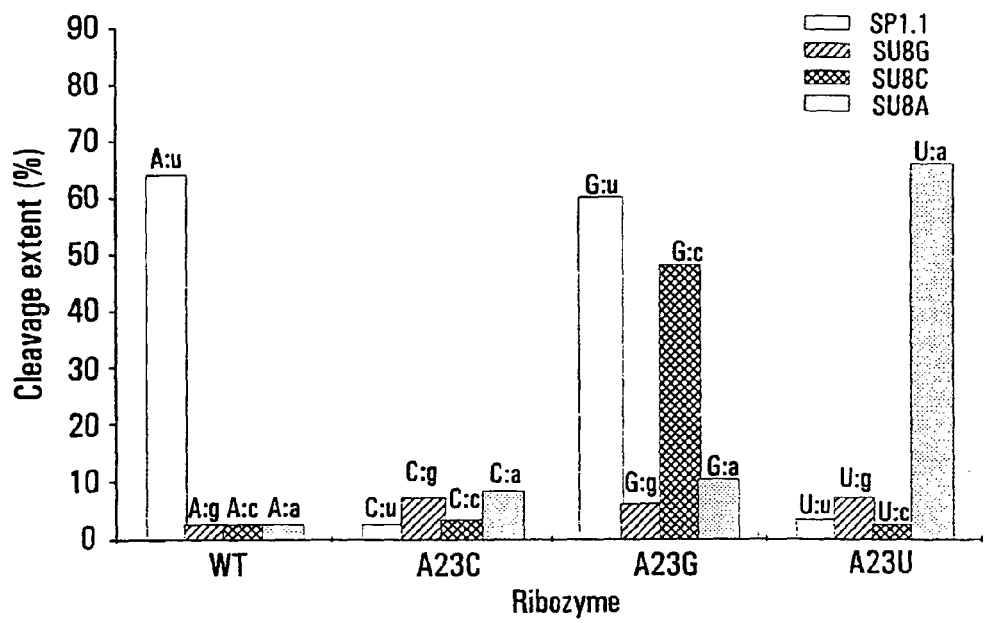
FIG. 5 shows results from Example 3, namely comparative analyses of the cleavage reactions catalyzed by delta ribozymes.
Figure 5B:
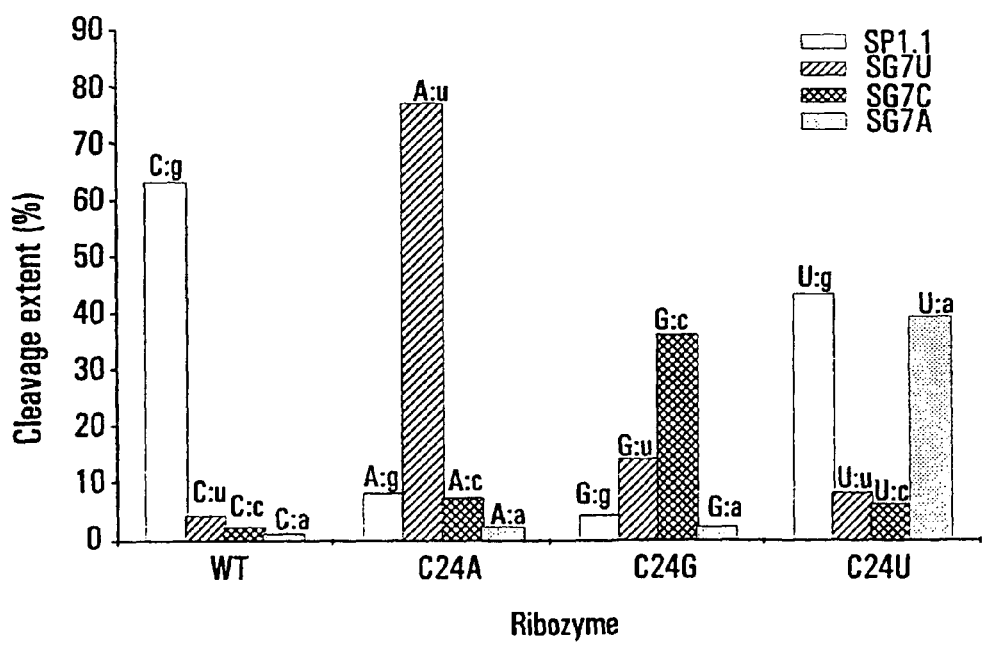

The extent of cleavage of the δRzP1-C24N ribozyme variants were compared with that of the wild type ribozyme δRzP1.1 for each of 4 substrates (A), and correspondingly, the extent of cleavage of the δRzP1-C24N ribozyme variants were compared with that of δRzP1.1 for each of the other 4 substrates (B). The results are shown in FIG. 5. The base pair formed between the ribozyme and the substrate is indicated by the capital and lower case letters, respectively, on each bar of the histogram. The values are an average calculated from at least two independent experiments.

Complementary pairs of substrates and ribozymes were used for kinetic studies to obtain the experimental data required for the calculation of apparent $K_m$ ($K_m'$) and apparent $k_2$ values and the results are shown in Table 4.

TABLE 4

Kinetic parameters for delta ribozymes. Under single turnover conditions, the cleavage rate ($k_2$) and the ribozyme concentration at the half velocity ($K_m'$) were determined. Calculated $K_d^{P1}$ values were based on the prediction of thermodynamic stability of the P1 stem duplex (13). $K_d^S$ and $K_d^P$ values were determined using end-labelled uncleavable substrate analogs and synthetic reaction products.

| Ribozyme | $k_2(\text{min}^{-1})$ | $K_m'(\text{nM})$ | $k_2/K_M$ ($\mu M^{-1}$ $\text{min}^{-1}$) | $k_{Mg}$ (mM) | $k_d^S$ (nM) | $k_d^P$ (nM) | Calculated $k_d^{P1}$ (nM) | $k_{-1}$ ($\text{min}^{-1}$) | Calculated $k_1$ ($\mu M^{-1}\text{min}^{-1}$) |
|---|---|---|---|---|---|---|---|---|---|
| δRzP1.1 | 0.34 ± 0.02 | 17.9 ± 5.6 | 19 | 2.2 ± 1 | 32 ± 3 | 42 ± 5 | 28.5 | 0.13 ± 0.03 | 4.0 |
| δRzP1-A23C[a] | 0.097 ± 0.01 | 15.5 ± 0.9 | 6 | b_ | 36 ± 5 | 45 ± 6 | 1.3 | ND | ND |
| δRzP1-A23G | 0.056 ± 0.01 | 14.8 ± 6.4 | 4 | 5.8 ± 1 | 36 ± 4 | 74 ± 9 | 1.3 | ND | ND |
| δRzP1-A23U | 0.19 ± 0.01 | 2.5 ± 0.4 | 76 | 1.9 ± 1.2 | 113 ± 20 | 17 ± 3 | 25.6 | 0.02 ± 0.01 | 0.17 |
| δRzP1-C24A | 0.26 ± 0.02 | 102 ± 13 | 3 | 2.4 ± 1 | 164 ± 22 | 648 ± 22 | 734.5 | 0.02 ± 0.01 | 0.12 |
| δRzP1-C24G | 0.23 ± 0.02 | 13.7 ± 8.6 | 17 | 2.5 ± 0.7 | 40 ± 10 | 68 ± 9 | 24.3 | 0.15 ± 0.01 | 3.7 |
| δRzP1-C24U | 0.087 ± 0.01 | 24.6 ± 11.1 | 4 | 5.1 ± 1.5 | 47 ± 8 | 73 ± 7 | 530.9 | ND | ND |

[a]Kinetic parameters were determined using end-labeled SU8G-9mer.
[b]The magnesium requirement could not be obtained by fitting the experimental data to the least squares equation.
ND represents non-determined values.
ii) Selection of a substrate comprising the sequence 5'-H' GNNHNN-3' or 5'-YHRH GNNHNNN-3'

A collection of 13 substrates including all single mutants for positions −4 to −1 compared to the original substrate were synthesized. Positions −4 to −1 refer to the four nucleotides directly 5' to the cleavage site, position −1 being right next to the cleavage site and position −4 being the furthest from the cleavage site, as shown in FIG. 2. For each mutant, trace amounts of 5'-$^{32}$P-labeled substrates (<1 nM) were incubated in the presence of an excess of ribozyme (200 nM), and the maximal cleavage percentages (i.e. end-point) (pre-steady state conditions) determined as a comparative parameter. The Applicant observed that the base requirement varies for each position. At position −1, the base preference was A>C>U>>G, where a guanosine at this position rendered the substrate uncleavable. At position −2, an A improved the cleavage efficiency compared to the original G, while a substrate with a U was poorly cleaved and a C gave an uncleavable substrate. In contrast at position −3, C, U and A gave substrates that have a two fold improved cleavage compared to the wildtype G. Finally at position −4, the presence of a pyrimidine (i.e. C or U) improved the maximal percentage of cleavage by at least two fold compared to a purine (i.e. G or A).

In order to assess accurately the base requirement at each position, kinetic analysis were performed under pre-steady-state conditions. Pseudo first-order cleavage rate constants ($k_2$ and $K_m'$) were measured with an excess of ribozyme (5 to 600 nM) and trace amounts of end-labeled substrate (<0.1 nM).

TABLE 5

Kinetic analysis of the collection of single mutated substrates. Pseudo first-order cleavage rate constants ($k_2$ and $K_m'$) were measured using an excess of ribozyme (5 to 600 nM) and trace amounts of end-labelled substrate (<0.1 nM). Apparent second-order rate constants ($k_2/K_m'$) were calculated and their relative specificity determined as compared to the original substrate. The values were calculated from at least two independent experiments, and errors were less than 25%. Sequence for position −4 to −1 are indicated for each substrate.

| Position | Identity | $K_M'$ (nM) | $k_2$ (min$^{-1}$) | $k_2/K_M'$ (nM$^{-1}$min$^{-1}$) | Specificity index |
|---|---|---|---|---|---|
| −1 | C | 31.52 | 0.22 | 6.66 × 10$^{-3}$ | 1.00 |
|    | U | 33.2 | 0.11 | 3.34 × 10$^{-3}$ | 0.50 |
|    | A | 14.27 | 0.27 | 1.79 × 10$^{-2}$ | 2.68 |
|    | G | na | na | na | na |
| −2 | G | 31.52 | 0.22 | 6.66 × 10$^{-3}$ | 1.00 |
|    | A | 28.7 | 0.33 | 1.15 × 10$^{-4}$ | 1.73 |
|    | C | na | na | na | na |
|    | U | 94 | 0.08 | 8.19 × 10$^{-4}$ | 0.12 |
| −3 | G | 31.52 | 0.22 | 6.66 × 10$^{-3}$ | 1.00 |
|    | A | 9.93 | 0.20 | 1.99 × 10$^{-2}$ | 3.02 |
|    | C | 11.3 | 0.24 | 2.10 × 10$^{-2}$ | 3.15 |
|    | U | 8.76 | 0.20 | 2.32 × 10$^{-2}$ | 3.48 |
| −4 | G | 31.52 | 0.22 | 6.66 × 10$^{-3}$ | 1.00 |
|    | A | 27.14 | 0.12 | 4.45 × 10$^{-3}$ | 0.67 |
|    | C | 11.81 | 0.27 | 1.86 × 10$^{-2}$ | 2.79 |
|    | U | 16.42 | 0.23 | 1.40 × 10$^{-2}$ | 2.10 |

Then, apparent second-order rate constants ($k_2/K_m'$) were calculated and a specificity index determined, fixing arbitrarily as 1.00 the original substrate (i.e. $_{-4}$GGGC$_{-1}$). At position −1, the presence of a uridine resulted in a similar relative specificity (0.50) while the presence of an adenine increased the relative specificity to 2.68. This increase appears mainly as a result of a $K_m'$ decrease of 2 fold. For position −2, the presence of a purine (i.e. G or A) gave similar relative specificity (1.73, compared to 1.00, respectively). In contrast, the presence of a uridine resulted in a poorly cleaved substrate, while when a cytosine was present, the substrate was uncleavable. In the case of the uridine at position −2, the specificity was evaluated to be reduced from 8 fold to 0.12 compared to the original substrate (i.e. 1.00). The decrease in specificity appears to result from a 3 fold increase of the $K_m'$ and a 3 fold decrease of the $k_2$ value. These results show a clear preference for purine in position −2, and a pyrimidine should be avoided in that position.

For position −3, when the guanosine of the original substrate was replaced by any other base (i.e. A, C, or U), the $K_m'$ was lowered by 3 fold while the $k_2$ remained almost identical, resulting in an specificity increase ranging from 3.02 to 3.48. Finally for position −4, a purine (G and A) yield a substrate with about the same specificity (i.e. 0.67 and 1.00). However, the presence of a pyrimidine in position −4 improved the specificity by at least two fold with 2.79 and 2.10 for a C and a U, respectively. Specifically, the presence of a C or a U the $K_m'$ was lowered, while the $k_2$ remained almost identical. Thus, it appears clear that the base requirement from position −4 to −1 of the substrate, contributes significantly and differently to the ability of the substrate to be cleaved.

Based on the observation that mutations in position −3 were those that most strongly increased the relative specificity, the Applicant investigated whether or not a larger amount of $Mg^{2+}$ in the cleavage reaction would affect the kinetic parameters of these substrates. Under single turnover conditions, in which the ribozyme and substrate concentrations were kept at 200 nM and 1 nM, respectively, the Applicant found that the ribozyme cleaved these substrates at $Mg^{2+}$ concentrations as low as 1 mM, which is the estimated physiological concentration of $Mg^{2+}$ (Ananovoranich, S. and Perreault, J. P. (1998) *J. Biol. Chem.*, 273, 13182–13188, and Trut, T. W. (1994) *Mol. Cell. Biochem.*, 140, 1–22). A maximum $k_{obs}$ for each substrate was observed when the concentration of $Mg^{2+}$ was 10 mM. The requirement for magnesium at half-maximal velocity ($K_{Mg}$) was similar for these mutated substrates and the original substrate, varying between 1.5 to 2.2 mM. Similar experiments were also performed with several other substrates from the collection and identical results were obtained, suggesting that the differences of the kinetic parameters for various substrates were not related to different affinity for the magnesium.

Notably, the cleavage assays performed with the initial collection of substrates (i.e. single mutants) indicated that the presence of a pyrimidine in the position −2 either reduces the cleavage activity or yields an uncleavable substrate. Specifically, a uridine decreases the relative specificity by 8 fold while a cytosine inhibits the cleavage completely (see Table 6). One plausible explanation of such results is that when a C is present at position −1 and followed by a pyrimidine (i.e. C or U) at position −2, both nucleotides of the substrate may interact with nucleotides located on the ribozyme resulting in inactive substrate/ribozyme complex. It seems reasonable to suggest that base-pairing may be formed with the ribozyme guanosines at position 27 and 28 of the J1/4 junction, which new base pairs will compete with formation of the P1.1 stem (FIG. 2). In this case, a cytosine in position −2 will form two consecutive GC base pairs. Similarly, a uridine in position −2 allows formation of a GC follow by a GU, which will be less stable than two GC's, yielding a reduced activity compared to the absence of activity. In order to learn more about the nucleotide preference in position −2, taking into account the neigboring positions, a second collection of substrates with more than one mutation were synthesized.

First, the Applicant verified whether a cytosine at position −2 after non-cytosine at position −1 has a detrimental effect. Based on the previous results, a substrate with an adenine in position −1 and a cytosine in position −2, $S-A_{-1}C_{-2}$, was synthesized and further tested for cleavage efficiency. A moderate extent of cleavage of 14% was observed at 200 nM ribozyme, which is less than the substrates including either the sequence $C_{-1}G_{-2}$ or $A_{-1}G_{-2}$. In comparison to the substrate with the sequence $A_{-1}G_{-2}$, the $S-A_{-1}C_{-2}$ substrate showed a virtually identical apparent $K_M$ ($K_M'$) while the cleavage constant ($k_2$) was reduced by approximately 4 fold, yielding a 4-fold reduction of the relative specificity (i.e. from 2.68 to 0.60; Table 6). These results suggest that the presence of a cytosine at position −2 reduces significantly the cleavage of a substrate. Moreover, if this cytosine is followed by a second cytosine in position −1, the result is an uncleavable RNA molecule (see above).

TABLE 6

Kinetic analysis of the collection of multiple mutated substrates. Pseudo first-order cleavage rate constants ($k_2$ and $K_m'$) were measured using an excess of ribozyme (5 to 600 nM) and trace amounts of end-labelled substrate (<0.1 nM). Apparent second-order rate constants ($k_2/K_m'$) were calculated and their relative specificity determined as compared to the original experiments, and errors were less than 25%. Sequence for position −4 to −1 are indicated for each substrate.

| Mutant | Km' (nM) | $k_2$ (min$^{-1}$) | $K_2/KM'$ (nM$^{-1}$min$^{-1}$) | Specificity index |
|---|---|---|---|---|
| $SC_{-1}G_{-2}$ | 31.5 | 0.22 | $6.98 \times 10^{-3}$ | 1 |
| $SA_{-1}$ | 14.3 | 0.27 | $1.89 \times 10^{-2}$ | 2.68 |
| $SA_{-1}C_{-2}$ | 15.4 | 0.06 | $3.9 \times 10^{-3}$ | 0.6 |
| $SA_{-1}C_{-2}C_{-3}$ | 15.2 | 0.039 | $2.57 \times 10^{-3}$ | 0.4 |
| $SA_{-1}C_{-2}C_{-3}C_{-4}$ | 16.5 | 0.25 | $1.52 \times 10^{-2}$ | 2.28 |

Secondly, the Applicant verified whether a cytosine at position −2 followed by a cytosine at position −3 gives a cleavable substrate. In other words, two consecutive cytosines, regardless of their positions, will yield uncleavable substrates. Therefore, the Applicant synthesized the substrate $S-A_{-1}C_{-2}C_{-3}$ and verified its ability to be cleaved. The $S-A_{-1}C_{-2}C_{-3}$ put together was cleaved with kinetic parameters almost identical to the the substrate $S-A_{-1}C_{-2}$ substrate except that the $k_2$ was slightly reduced to 0.039 min$^{-1}$ compared to 0.062 min$^{-1}$, resulting in a small reduction of the relative specificity (i.e. from 0.60 to 0.40; Table 6). These results show that the presence of a cytosine at position −3 following a cytosine at position −2 reduced slightly the cleavage activity, and did not significantly modify the ability of a substrate to be cleaved. Thus, a cytosine at position −3 does not have the same influence as that at position −2.

Thirdly, the Applicant asked whether two consecutive cytosines at positions −4 and −3 give a similar effect yielding uncleavable (or less cleaved) substrate. A substrate containing cytosines at positions −3 and −4 and adenines in position −1 and −2 was synthesized. Adenines were included in position −1 and −2 because this residue appears to give a readily cleaved substrate as compared to the single mutation collection (see above). The $S-A_{-1}A_{-2}C_{-3}C_{-4}$ mutant has a maximum cleavage of 61%. Moreover, the Applicant determined a $K_M'$ of 16.5 nM and a $k_2$ value increased to 0.25 min$^{-1}$, resulting in a substrate with a relative specificity of 2.28 as compared to the original substrate (Table 6). Thus, the presence of two consecutive cytosines at position −3 and −4 has no detrimental effect.

Finally, the Applicant asked whether it is possible to compensate for the detrimental effect of the presence of two consecutive cytosines at positions −1 and −2, by including the one at position −2 in a hairpin structure. A longer RNA substrate (i.e. 18-mer compared to 14mer) including a hairpin at 5'-end, which involved the $C_{-2}$ in the last base pair of the helix was chemically synthesized and then tested. This substrate was poorly cleaved. Only trace amounts of products were detected (i.e. maximum percentage cleavage of <2.0%), and as a consequence, no more extensive characterization was possible. If the sequence was drawn in order to avoid the formation of the 5'-end hairpin (i.e. $C_{-2}$ remains single strand; S-hp-), no cleavage at all was observed. These two results showed that the presence of a base-paired cytosine at position −2 gave minimal activity as compared to this cytosine in single strand. However, the improvement was very limited.

Example 4

L4 Loop Modifications

A modified form of δRzP1.1 described above was made by replacing the L4 loop sequence GCUU which is relatively unstable, with the ultrastable L4 loop (UUCG) (shown on the right in FIG. 3). The kinetic parameters ($k_{cat}$ and $K_M$) and dissociation constant ($K_d$) were virtually identical.

Example 5

Bimolecular Ribozyme

A modified form of δRzP1.1 described above was made by dividing the L4 loop into two resulting in two fragments, namely, RzA and RzB (as shown in FIG. 4). The RzA consists of 37 nucleotides encompassing a substrate recognition site (P1 stem), P3 stem and portions of P2 and P4 stems. The RzB consists of 20 nucleotides which is able to base pair to RzA to form a bimolecular ribozyme complex. RzA and RzB were synthesized as described in Example 1. Because both RzA and RzB are relatively small, they can be chemically synthesized. Therefore, this bimolecular delta ribozyme allows the introduction of any chemically modified nucleoside.

Example 6

Deoxyribonucleotide Modifications

Example 5 describes a bimolecular ribozyme. Modified versions of the ribozyme described in Example 5 were made by replacing one ribonucleotide in RzB with a deoxyribonucletide individually at positions 9 to 15. This resulted in 7 different RzB's each containing one deoxyribonucleic acid.

Figure 6:
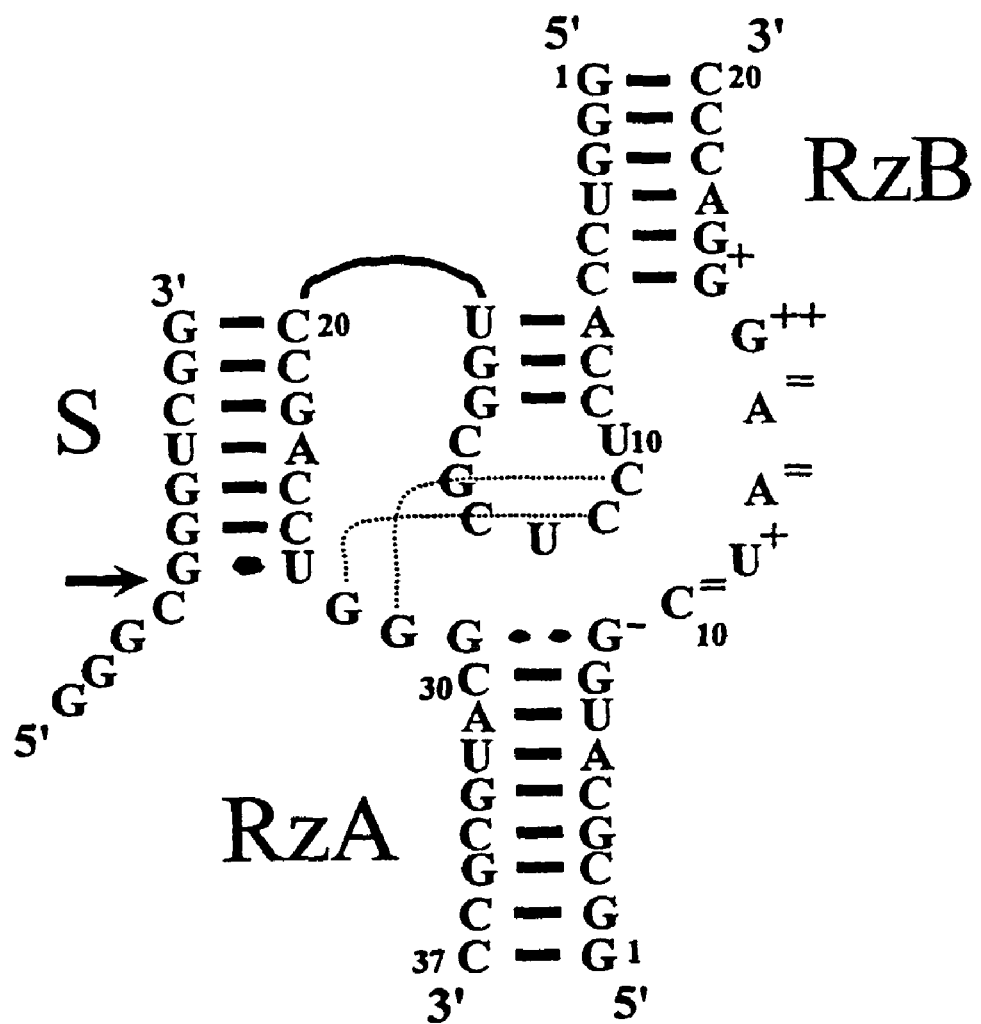
FIG. 6 shows a two-dimensional representation of a catalytic trimolecular complex (RzA:RzB:S); the influence of 2'-OH groups individually at positions 9 to 15 on RzB by replacing the ribonucleotide at these positions with the corresponding deoxy-ribonucleotide is shown; the symbol – represents a two-fold diminution of activity compared to an unmodified RzB while the symbol = represents an unchanged catalytic activity; symbols + and ++ respectively represent an increased activity of 1.5- and 2-fold; horizontal bars represent base pairs; wobble and homopurine base pairs are respectively represented by one and two ovals; the arrow indicates the site of catalytic cleavage.

The influence of 2'-OH groups in RzB on the catalytic activity of RzA:RzB complex was analyzed. 0.066 uM of a mix of cold and end-labeled RNA substrates were incubated in presence of 0.066 uM of RzA and 0.2 uM of various RzB RNA/DNA mixed polymers. The incubation was performed in 50 uM Tris-HCl pH 8.0 and 50 mM $MgCl_2$ at 37° C. An aliquot was removed after one hour and the reaction stopped by the addition of an excess of stop solution (xc, bb, formamide). Reaction mixtures were fractioned on 20% polyacrylamide gel electrophoresis and were exposed on x-ray films. Fully deoxyribonucleotide RzB molecules are not able to support a cleavage activity. Individual deoxy substitution mutants were subjected to catalytic cleavage. All of the reconstituted complexes were active to different extents. S and P respectively represent substrate and product species. As an example, dGg stands for GGCGCAUGgC-UAAGGGACCC (SEQ ID: 55) where uppercase and lowercase letters respectively represent ribo- and deoxyribo-nucleotides. The results are shown in FIG. 6 and Table 7.

Table 7 shows the quantification of time course experiments performed. Rate and extent of cleavage values were obtained from fitting the experimental data to the equation $A_t = A_{alpha}(1-e-kt)$ where $A_t$ is the percentage of cleavage at time, t, $A_{alpha}$ is the maximum cleavage and k is the reaction rate. Data analysis was performed with GraFit Version 3.01 from Erithacus Software.

TABLE 7

Rate and extent of substrate cleavage using 2'-OH modified ribozymes.

| Species | Rate (min$^{-1}$) | Extent (%) |
|---|---|---|
| RzB | 5.7 × 10$^{-2}$ | 27.01 |
| dG9 | 3.3 × 10$^{-2}$ | 9.80 |
| dC10 | 2.4 × 10$^{-2}$ | 30.42 |
| dU11 | 4.6 × 10$^{-2}$ | 45.87 |
| dA12 | 4.0 × 10$^{-2}$ | 26.79 |
| dA13 | 1.8 × 10$^{-2}$ | 27.46 |
| dG14 | 8.0 × 10$^{-2}$ | 61.44 |
| dG15 | 7.8 × 10$^{-2}$ | 54.15 |

FIG. 6 illustrates the sequence of the ribozymes of this Example and shows the efficiency of cleavage of the substrate molecules as a function of the position of the deoxyribonucleic acid.

Example 7

Cleavage of HDAg mRNA

Plasmids encoding the HDAg mRNA and delta ribozymes. The pKSAgS plasmid carries the S-HDAg mRNA in pBluescript KS+ (Stratagene). Briefly, the S-HDAg mRNA insert (positions 900 to 1679 of the vHDV.5 variant (according to Lafontaine, D., Mercure, S. and Perreault, J. -P. (1997) Nucleic Acids Res., 25, 123–125) were retrieved by PCR amplification using pSVL(AgS) (Chao, M., Hsieh, S. Y. and Taylor, J. (1990) J. Virol., 64, 5066–5069) as template. The oligonucleotides used in this PCR had restriction sites situated at their 5' ends so as to facilitate subsequent cloning: HDV1679.66: 5'CC GGATCCCTCGGGCTCGGGCG 3' (SEQ ID: 41) (underlined is the Bam H1 restriction site) and HDV900.914: 5'CC AAGCTTCGAAGAGGAAAGAAG 3' (SEQ ID: 42) (underlined is the Hind III restriction site). Plasmid DNA (pSVL(AgS), 50 ng), 0.4 mM of each oligonucleotide, 200 mM dNTPs, 1.25 mM $MgCl_2$, 10 mM Tris-HCl pH 8.3, 50 mM KCl, and 1 U Taq DNA polymerase were mixed together in a final volume of 100 μL. The Applicant performed one low stringent PCR cycle (94° C. for 5 min, 53° C. for 30 s, 72° C. for 1 min), followed by 35 cycles at higher stringency (94° C. for 1 min, 62° C. for 30 s, 72° C. for 1 min). The mixture was fractionated by electrophoresis in a 1% agarose gel in 1× TBE buffer (90 mM Tris-borate, 2 mM EDTA pH 8.0), the expected band excised and eluted using the QIAquick gel extraction kit (Qiagen), and finally digested and ligated into pBluescript KS+. The strategy used for the construction of plasmids carrying ribozymes with modified substrate recognition domains is described above. All constructs were verified by DNA sequencing.

RNA Synthesis. In vitro transcription: HDAg mRNA was transcribed from Hind III-linearized pKSAgS, while ribozymes were transcribed from Sma I-linearized ribozyme encoding plasmids as described in Example 1. Small substrates (11-nt) were synthesized as described in Example 1.

Oligonucleotide probing. DNA oligonucleotides complementary to the potential target sites were purchased from Gibco-BRL and 5'-end labelled using T4 polynucleotide kinase (Pharmacia) in the presence of 10 μCi [γ-$^{32}$P]ATP. Labelled oligonucletiodes (~2 500 cpm; ~0.05 nM) and unlabelled mRNA (2.4 to 1 200 nM) were hybridized together for 10 min at 25° C. in a solution containing 50 mM Tris-HCl pH 7.5 and 10 mM MgCl$_2$ in a final volume of 15 μL. Loading solution (2 μL of 1× TBE, 10 MM MgCl$_2$, 40% glycerol, 0.25% bromophenol blue and 0.25% xylene cyanol) was added, and the resulting solutions fractionated on native 5% PAGE gels (30:1 ratio of acrylamide to bisacrylamide, 50 mM Tris-borate pH 8.3, 10 mM MgCl$_2$ and 5% glycerol) at 4° C. in the presence of recirculating 50 mM Tris-borate pH 8.3 and 10 mM MgCl$_2$ buffer. The dried gels were analyzed with the aid of a PhosphorImager (Molecular Dynamics). RNase H probing was performed using the same oligonucleotides. In these experiments randomly labelled S-HDAg mRNA (~10 000 cpm; ~10 nM) and unlabelled oligonucleotides (1 μM) were annealed as described for gel shift assays for 10 min, then 0.2 U of *E. coli* RNase H (Pharmacia) was added and the reaction incubated at 37° C. for 20 min. The reactions were stopped by the addition of stop-solution (3 μL of 97% formamide, 10 mM EDTA, 0.25% bromophenol blue and 0.25% xylene cyanol), fractionated on 5% denaturing PAGE gels, and analyzed by autoradiography.

In vitro cleavage assays and kinetic analyses. Cleavage assays were performed at 37° C. under single turnover conditions with either randomly labelled mRNA (~10 nM) or 5'-end labelled small substrates (<1 nM), and an excess of ribozyme (2,5 μM) in a 10 μL final volume containing 50 mM Tris-HCl pH 8.0 and 10 mM MgCl$_2$. A pre-incubation of 5 min at 37° C. preceeded the addition of the Tris-magnesium buffer which initiates the reaction. After an incubation of 1 to 3 hrs at 37° C., stop-solution (5 μl) was added and the mixture quickly stored at −20° C. until its fractionation on 5% denaturing PAGE gels and subsequent autoradiography. Cleavage sites of the active ribozymes were verified by primer extension assays as described previously (Côté, F. and Perreault, J. -P. (1997) J. Mol. Biol., 273, 533–543). Briefly, oligonucleotides were synthesized to have complementary sequence to positions downstream (~100 positions) from the cleavage site according to the mRNA. For example, for the cleavage site of Rz-12, the oligonucleotide primer, 5'CTTTGATGTTCCCCAGC-CAGG-3' (SEQ ID: 56) (21mer), was used in the reverse transcriptase reaction containing the ribozyme cleavage reaction mixture.

Active ribozymes (Rz-1, -11 and -12) were characterized under single turnover conditions essentially as described in Example 1.

TABLE 8

Synthesized delta ribozyme.

| Ribozyme | P1 Stem sequence | Size of expected cleavage products (nt) |
|---|---|---|
| Rz-1 | CCCAGCU | 265, 551 |
| Rz-2 | CCUCUUU | 330, 486 |
| Rz-3 | CCUUGUU | 403, 413 |
| Rz-4 | UGUUCUU | 440, 376 |
| Rz-6 | GGGGUUU | 572, 244 |
| Rz-7 | UCCCCUU | 593, 223 |
| Rz-9 | GGACUCU | 640, 176 |
| Rz-11 | UCGACUU | 130, 686 |
| Rz-12 | GCCACCU | 175, 641 | mRNA sequence (SEQ ID:43)
mRNA sequence

```
  1 CACCGCGGU GCGGCCGC UAGAACUAG GGAUCCCU GGCUCGGGCG GCGAGUCC

61 CAGUCUCCU UUUACAGA AUGUAAGAG ACUGAGGA GCCGCCUCUA GCCGAGAU

121 GCCGGUCCG GUCGAGGA AACCGCGGA GGAGAGAA GAUCCUCGAG CAGUGGGU    (11, 12)

181 CCGGAAGAA GAAGUUAG GAACUCGAG GAGACCUC GAAGACAAAG AAGAAACU

241 AGAAGAUAG GGACGAAA CCCUGGCUG GGAACAUC AGGAAUUCUC GGAAAGAA    (1)

301 AUAAGGAUG AGAGGGGG CCCCCCGCG AGAGGGCC AACGGACCAG AUGGAGGU    (2)

361 ACUCCGGAC UCGGAAGA CCUCUCAGG GAGGAUUC CGACAAGGAG AGGCAGGA    (3)

421 CCGACGAAG AAGGCCCU AGAACAAGA GAAGCAGC UCGGCGGGAG GCAAGAAC    (4)

481 CAGCAAGGA GAAGAAGA AACUCAGGA GUUGACCG GAAGACGAGA GAAGGGAA

541 AAGAGUAGC GGCCCGCC UUGGGGGUG GAACCCCC GAAGGUGGAU CGAGGGGA    (6, 7)

601 GCCCGGGGG GGCUUCGU CCAAUCUGC GGGAGUCC GAGUCCCCU UCUCUCGG     (9)
```

TABLE 8-continued

Synthesized delta ribozyme.

```
661 CGGGGAGGG CUGGACAU GGGGAAACC GGGAUUUC UAGGAUAUAC UCUUCCCA

721 CGAUCCGCC UUUUCUCC AGAGUUGUC ACCCCAGU AUAAAGCGGG UUUCCACU

781 CAGGUUUGC UCUCGCGU UUCUUUCCU UUC
```

Previous page is the ribozyme nomenclature with the sequence composing the P1 stem domain and the size of the expected products. This page is the mRNA sequence. The mRNA sequences targeted by ribozymes are underlined, and the ribozyme number is in parentheses on the right.

Of the nine ribozymes examined, three, namely Rz1, Rz11, and Rz12, specifically cleaved a derivative HDV mRNA. The most active ribozyme under steady-state conditions, displaying multiple turnovers, was Rz-12. As can be observed from Table 8, the sequence of the substrate for this ribozyme (positions 87–97) is 5' CAGU GGGUGG-3'. This accords with the sequence preferences shown in Table 5.

Example 8

Figure 7A:
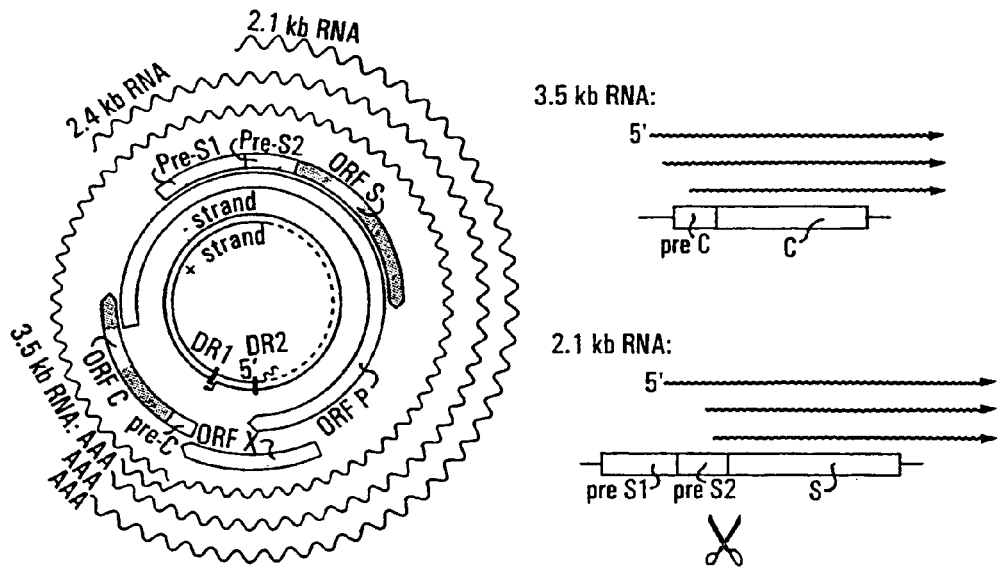
FIG. 7 shows in Panel A the structural and functional features of virion DNA, including the viral direct repeat (DR) sequences (boxed), and the protein (•) and RNA (ΛΛΛ) species found at the 5' ends of the minus and plus DNA strands, respectively; the dashed line indicates the presence of the single stranded gap; the RNA products are depicted by wavy lines; the target area is located in pre-S2 and S regions, and is indicated by the scissors symbol; panel B illustrates the secondary struction of an engineered ribozyme of the the invention, such that the substrate binding region is 5' GGGAUAU-3', complementary to HBV mRNA substrates.
Figure 7B:
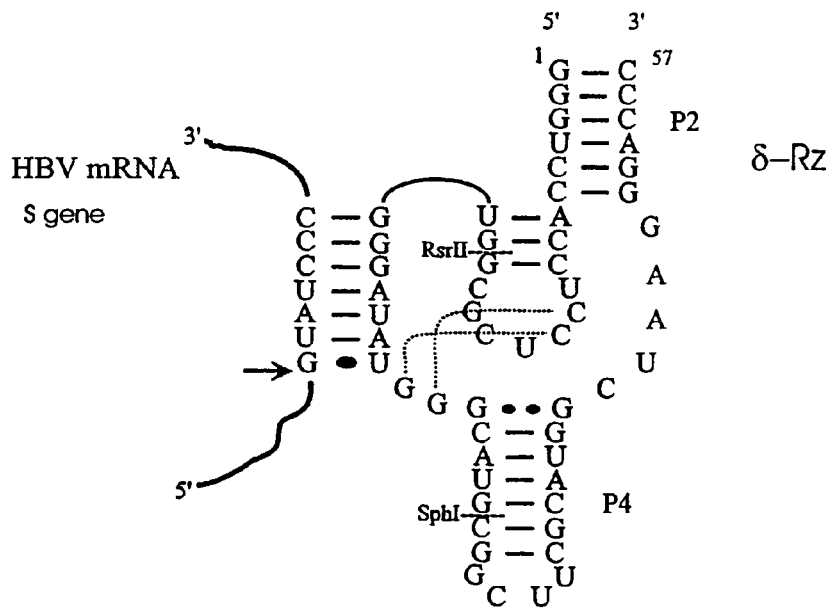

Cleavage Assay of a Ribozyme of the Invention Against 552 nt-HBV RNA Substrate 500 nM of a delta ribozyme as shown in FIG. 7 was incubated with 1 nM randomly-labelled 552 nt-HBV (human hepatitis B virus) mRNA at 37° C. in the presence of 50 mM Tris-HCl pH 7.5 and 10 mM $MgCl_2$. A single exponential equation was used to fit data to $k_{obs}=0.031$ $min^{-1}$ with 28% cleavage. This demonstrates that a ribozyme of the invention cleaves mRNA from the human hepatitis B virus.

---

We claim:

1. A nucleic acid enzyme capable of recognizing and cleaving a nucleic acid substrate, said nucleic acid enzyme which when bound to the substrate comprises:
   (i) a first nucleotide sequence 5'-$G^1G^2G^3U^4C^5C^6A^{13}C^{14}C^{15}UC^{16}C^{17}UCGCG^{15}G^{14}U^{13}N^1N^2N^3N^4N^5N^6N^7G^{17}G^{16}G^7C^8A^9U^{10}G^{11}C^{12}S^1B^1Y$-3' (SEQ ID NO: 65); and
   (ii) a second nucleotide sequence 5'-$B^2KS^2G^{12}C^{11}A^{10}U^9G^8G^7CUAAGG^6G^5A^4C^3C^2C^1$-3' (SEQ ID NO: 66);

wherein non-variable nucleotides having the same superscript form conventional Watson-Crick base pairs, except the two $G^7$ form a homopurine base pair;
$S^1$ and S2 are each independently selected from the group consisting of G and C;
$B^1$ and $B^2$ are each independently selected from the group consisting of G, C, U and T;
K is selected from the group consisting of G, U and T;
Y is selected from the group consisting of C, U and T;
$S^1$ and $S^2$ form a conventional Watson-Crick base pair;
Y and $B^2$ may form a conventional Watson-Crick base pair;
$B^1$ and K may form a conventional Watson-Crick base pair;
$B^1$, K, Y and $B^2$ may together form a loop;
$N^1N^2N^3N^4N^5N^6N^7$ forms a substrate binding region;
$N^1$, $N^2$, $N^3$, $N^4$, $N^5$ and $N^6$ are each a nucleotide which may be the same or different;
$N^7$ is U;
$N^7$ is capable of forming a wobble pair with the substrate;
$N^1$, $N^2$, $N^3$, $N^5$ and $N^6$ are capable of forming conventional Watson-Crick base pairs with the substrate; and
$N^4$ is capable of forming a non-conventional Watson-Crick base pair and a conventional Watson-Crick base pair.

2. The nucleic acid enzyme of claim 1, wherein said enzyme comprises a nucleotide sequence selected from the group consisting of:
   (i) 5'-$G^1G^2G^3U^4C^5C^6A^{13}C^{14}C^{15}UC^{16}C^{17}UCGCG^{15}G^{14}U^{13}N^1N^2N^3N^4N^5N^6N^7G^{17}G^{16}G^7C^8A^9U^{10}G^{11}C^{12}G^{18}GCUUC^{18}G^{12}C^{11}A^{10}U^9G^8G^7CUAAGG^6G^5A^4C^3C^2C^1$-3' (SEQ ID NO: 61); and
   (ii) 5'-$G^1G^2G^3U^4C^5C^6A^{13}C^{14}C^{15}UC^{16}C^{17}UCGCG^{15}G^{14}U^{13}N^1N^2N^3N^4N^5N^6N^7G^{17}G^{16}G^7C^8A^9U^{10}G^{11}C^{12}C^{18}UUCGG^{18}G^{12}C^{11}A^{10}U^9G^8G^7CUAAGG^6G^5A^4C^3C^2C^1$-3' (SEQ ID NO: 62).

3. The nucleic acid enzyme of claim 1, wherein said first nucleotide sequence is 5'-$G^1G^2G^3U^4C^5C^6A^{13}C^{14}C^{15}UC^{16}C^{17}UCGCG^{15}G^{14}U^{13}N^1N^2N^3N^4N^5N^6N^7G^{17}G^{16}G^7C^8A^9U^{10}G^{11}C^{12}G^{18}C^{19}C^{20}$-3' (SEQ ID NO: 63) and said second nucleotide sequence is 5'-$G^{20}G^{19}C^{18}G^{12}C^{11}A^{10}U^9G^8G^7CUAAGG^6G^5A^4C^3C^2C^1$-3' (SEQ ID NO: 64).

4. The nucleic acid of claim 1, wherein $N^1N^2N^3N^4N^5N^6N^7$ is selected from the group consisting of:
   (i) CCGACCU;
   (ii) CCCAGCU;
   (iii) GGGAUAU;
   (iv) CCGCCCU;
   (v) CCGGCCU;
   (vi) CCGUCCU;
   (vii) CCGAACU;
   (viii) CCGAGCU;
   (ix) CCGAUCU;
   (x) CCUCUUU;
   (xi) CCUUGUU;
   (xii) UGUUCUU;
   (xiii) GGGGUUU;
   (xiv) UCCCCUU;
   (xv) GGACUCU;
   (xvi) UCGACUU; and
   (xvii) GCCACCU.

5. The nucleic acid enzyme of claim 1, wherein the enzyme is derived from hepatitis delta virus.

6. The nucleic acid enzyme of claim 1, wherein the enzyme is composed of ribonucleotides.

7. The nucleic acid enzyme of claim 1, wherein the enzyme is composed of a mixture of ribonucleotides and deoxyribonucleotides.

8. A method for cleaving a nucleic acid substrate with a nucleic acid enzyme comprising mixing said substrate with the nucleic acid enzyme of claim 1.

9. The nucleic acid enzyme of claim 1, wherein $G^{16}$ and $G^{17}$ are incapable of forming a bond with the substrate.

10. A nucleic acid enzyme capable of recognizing and cleaving a nucleic acid substrate, said nucleic acid enzyme which when bound to the substrate comprises:
    (i) a first nucleotide sequence 5'-$G^1G^2G^3U^4C^5C^6A^{13}C^{14}C^{15}UC^{16}C^{17}UCGCG^{15}G^{14}U^{13}N^1N^2N^3N^4N^5N^6N^7G^{17}G^{16}G^7C^8A^9U^{10}G^{11}C^{12}S^1B^1Y$-3' (SEQ ID NO: 65); and
    (ii) a second nucleotide sequence 5'-$B^2KS^2G^{12}C^{11}A^{10}U^9G^8G^7CUAAGG^6G^5A^4C^3C^2C^1$-3' (SEQ ID NO: 66);

wherein non-variable nucleotides having the same superscript form conventional Watson-Crick base pairs, except the two $G^7$ form a homopurine base pair;
$S^1$ and $S^2$ are each independently selected from the group consisting of G and C;
$B^1$ and $B^2$ are each independently selected from the group consisting of G, C, U and T;
K is selected from the group consisting of G, U and T;
Y is selected from the group consisting of C, U and T;
$S^1$ and $S^2$ form a conventional Watson-Crick base pair;
Y and $B^2$ may form a conventional Watson-Crick base pair;
$B^1$ and K may form a conventional Watson-Crick base pair;
$B^1$, K, Y and B may together form a loop;
$N^1N^2N^3N^4N^5N^6N^7$ forms a substrate binding region;
$N^1$, $N^2$, $N^3$, $N^4$, $N^5$ and $N^6$ are each a nucleotide which may be the same or different;
$N^7$ is U;
$N^7$ is capable of forming a wobble pair with the substrate;
$N^1$, $N^2$, $N^3$, $N^5$ and $N^6$ are capable of forming conventional Watson-Crick base pairs with the substrate; and
$N^4$ is capable of forming a non-conventional Watson-Crick base pair and a conventional Watson-Crick base pair,
wherein the enzyme is incapable of forming a bond with the nucleotide residues of said substrate in positions −1 and −2 directly 5' to the cleavage site.

11. A nucleic acid enzyme capable of recognizing and cleaving a nucleic acid substrate, said nucleic acid enzyme which when bound to the substrate comprises:
    (i) a first nucleotide sequence 5'-$G^1G^2G^3U^4C^5C^6A^{13}C^{14}C^{15}UC^{16}C^{17}UCGCG^{15}G^{14}U^{13}N^1N^2N^3N^4N^5N^6N^7G^{17}G^{16}G^7C^8A^9U^{10}G^{11}C^{12}S^1B^1Y$-3' (SEQ ID NO: 65); and
    (ii) a second nucleotide sequence 5-$B^2KS^2G^{12}C^{11}A^{10}U^9G^8G^7CUAAGG^6G^5A^4C^3C^2C^1$-3' (SEQ ID NO: 66);

wherein non-variable nucleotides having the same superscript form conventional Watson-Crick base pairs, except the two $G^7$ form a homopurine base pair;
$S^1$ and $S^2$ are each independently selected from the group consisting of G and C;

$B^1$ and $B^2$ are each independently selected from the group consisting of G, C, U and T;
K is selected from the group consisting of G, U and T;
Y is selected from the group consisting of C, U and T;
$S^1$ and $S^2$ form a conventional Watson-Crick base pair;
Y and $B^2$ may form a conventional Watson-Crick base pair;
$B^1$ and K may form a conventional Watson-Crick base pair;
$B^1$, K, Y and $B^2$ may together form a loop;
$N^1N^2N^3N^4N^5N^6N^7$ forms a substrate binding region;
$N^1$, $N^2$, $N^3$, $N^4$, $N^1$ and $N^6$ are each a nucleotide which may be the same or different;
$N^7$ is U;
$N^7$ is capable of forming a wobble pair with the substrate;
$N^1$, $N^2$, $N^3$, $N^5$ and $N^6$ are capable of forming conventional Watson-Crick base pairs with the substrate; and
$N^4$ is capable of forming a non-conventional Watson-Crick base pair and a conventional Watson-Crick base pair,
wherein the enzyme is adapted to bind to the substrate such that the enzyme is incapable of interacting with nucleotide residues in the substrate at positions −1 and −2 directly 5' to the cleavage site and the enzyme is capable of forming a GU wobble pair with the nucleotide residue (G) in the substrate directly 3' to the cleavage site.

* * * * *

SEQUENCE LISTING

```
<160> NUMBER OF SEQ ID NOS: 66

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence:  nucleotide
      sequence comprised of ribonucleotides or a
      combination of ribonucleotides and
      deoxyribonucleotides
<220> FEATURE:
<221> NAME/KEY: misc_feature
<222> LOCATION: (1) ... (11)
<223> OTHER INFORMATION: n is a or g or c or t/u, unknown, or other

<400> SEQUENCE: 1
nnrhgnnhnn n                                                                11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence:  nucleotide
      sequence comprised of ribonucleotides or a
      combination of ribonucleotides and
      deoxyribonucleotides
<220> FEATURE:
<221> NAME/KEY: misc_feature
<222> LOCATION: (6) ... (11)
```

<223> OTHER INFORMATION: n is a or g or c or t/u, unknown, or other

<400> SEQUENCE: 2
rrrhgnnhnn n                                                         11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence:  nucleotide
      sequence comprised of ribonucleotides or a
      combination of ribonucleotides and
      deoxyribonucleotides
<220> FEATURE:
<221> NAME/KEY: misc_feature
<222> LOCATION: (6) ... (11)
<223> OTHER INFORMATION: n is a or g or c or t/u, unknown, or other

<400> SEQUENCE: 3
gggcgnnunn n                                                         11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence:  nucleotide
      sequence comprised of ribonucleotides or a
      combination of ribonucleotides and
      deoxyribonucleotides
<220> FEATURE:
<221> NAME/KEY: misc_feature
<222> LOCATION: (6) ... (11)
<223> OTHER INFORMATION: n is a or g or c or t/u, unknown, or other

<400> SEQUENCE: 4
gggcgnnhnn n                                                         11

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence:  nucleotide
      sequence comprised of ribonucleotides or a
      combination of ribonucleotides and
      deoxyribonucleotides
<220> FEATURE:
<221> NAME/KEY: misc_feature
<222> LOCATION: (6) ... (11)
<223> OTHER INFORMATION: n is a or g or c or t/u, unknown, or other

<400> SEQUENCE: 5
gggugnnunn n                                                         11

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence:  nucleotide
      sequence comprised of ribonucleotides or a
      combination of ribonucleotides and
      deoxyribonucleotides
<220> FEATURE:
<221> NAME/KEY: misc_feature
<222> LOCATION: (6) ... (12)
<223> OTHER INFORMATION: n is a or g or c or t/u, unknown, or other

<400> SEQUENCE: 6
gggugnncnn nn                                                              12

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: nucleotide
      sequence comprised of ribonucleotides or a
      combination of ribonucleotides and
      deoxyribonucleotides
<220> FEATURE:
<221> NAME/KEY: misc_feature
<222> LOCATION: (6) ... (11)
<223> OTHER INFORMATION: n is a or g or c or t/u, unknown, or other

<400> SEQUENCE: 7
aaacgnnunn n                                                               11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: nucleotide
      sequence comprised of ribonucleotides or a
      combination of ribonucleotides and
      deoxyribonucleotides
<220> FEATURE:
<221> NAME/KEY: misc_feature
<222> LOCATION: (6) ... (11)
<223> OTHER INFORMATION: n is a or g or c or t/u, unknown, or other

<400> SEQUENCE: 8
yhrhgnnhnn n                                                               11

<210> SEQ ID NO 9
<211> LENGTH: 11
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 9
gggcgggucg g                                                               11

<210> SEQ ID NO 10
<211> LENGTH: 10
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 10
gggcgggucg                                                                 10

<210> SEQ ID NO 11
<211> LENGTH: 11
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 11
gggcaggucg g                                                               11

```
<210> SEQ ID NO 12
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 12
gggccggucg g                                                              11

<210> SEQ ID NO 13
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 13
gggcgagucg g                                                              11

<210> SEQ ID NO 14
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 14
gggcgugucg g                                                              11

<210> SEQ ID NO 15
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 15
gggcggaucg g                                                              11

<210> SEQ ID NO 16
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 16
gggcgguucg g                                                              11

<210> SEQ ID NO 17
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 17
gggcgggccg g                                                              11
```

```
<210> SEQ ID NO 18
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 18
gggcggggcg g                                                              11

<210> SEQ ID NO 19
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 19
gggcggguag g                                                              11

<210> SEQ ID NO 20
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 20
gggcggguug g                                                              11

<210> SEQ ID NO 21
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 21
gggcgggucu g                                                              11

<210> SEQ ID NO 22
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 22
gggcgggucg u                                                              11

<210> SEQ ID NO 23
<211> LENGTH: 11
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 23
gggcggcucg g                                                              11
```

```
<210> SEQ ID NO 24
<211> LENGTH: 11
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 24
gggcgggacg g                                                           11

<210> SEQ ID NO 25
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 25
ggagggcggg ucgg                                                        14

<210> SEQ ID NO 26
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 26
ggaggggggg ucgg                                                        14

<210> SEQ ID NO 27
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 27
ggacggcggg ucgg                                                        14

<210> SEQ ID NO 28
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 28
ggaggccggg ucgg                                                        14

<210> SEQ ID NO 29
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 29
ggaaggcggg ucgg                                                        14

<210> SEQ ID NO 30
```

```
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 30
ggagagcggg ucgg                                                       14

<210> SEQ ID NO 31
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 31
ggaggacggg ucgg                                                       14

<210> SEQ ID NO 32
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 32
ggagggaggg ucgg                                                       14

<210> SEQ ID NO 33
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 33
ggauggcggg ucgg                                                       14

<210> SEQ ID NO 34
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 34
ggagugcggg ucgg                                                       14

<210> SEQ ID NO 35
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 35
ggaggucggg ucgg                                                       14

<210> SEQ ID NO 36
<211> LENGTH: 14
```

```
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 36 ggagggugggg ucgg                                                         14

<210> SEQ ID NO 37
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 37
ggagggaggg ucgg                                                          14

<210> SEQ ID NO 38
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 38
ggaggcaggg ucgg                                                          14

<210> SEQ ID NO 39
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 39
ggagccaggg ucgg                                                          14

<210> SEQ ID NO 40
<211> LENGTH: 14
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 40
ggaccaaggg ucgg                                                          14

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: DNA PCR
      primer

<400> SEQUENCE: 41
ccggatccct cgggctcggg cg                                                 22

<210> SEQ ID NO 42
<211> LENGTH: 23
<212> TYPE: DNA
```

```
<213> ORGANISM: Artificial Sequence
<220> FEATURE:
<223> OTHER INFORMATION: Description of Artificial Sequence:  DNA PCR
      primer

<400> SEQUENCE: 42
ccaagcttcg aagaggaaag aag                                              23

<210> SEQ ID NO 43
<211> LENGTH: 813
<212> TYPE: RNA
<213> ORGANISM: Human Delta Virus

<400> SEQUENCE: 43
caccgcggug gcggccgcuc uagaacuagu ggaucccucg ggcucgggcg gcgaguccag       60 cagucccuc uuuacagaaa auguaagagu acugaggacu gccgcucua gccgagauga       120 gccgguccga gucgaggaag aaccgcggag ggagagaaga gauccucgag cagugggugg      180
ccggaagaaa gaaguuagag gaacucgaga gagaccuccg gaagacaaag aagaaacuca      240
agaagauaga ggacgaaaau cccuggcugg ggaacaucaa aggaauucuc ggaaagaagg      300
auaaggaugg agaggggcu cccccgcga agagggcccg aacggaccag auggagguag        360
acuccggacc ucggaagagg ccucucaggg gaggauucac cgacaaggag aggcaggauc      420
ccgacgaagg aaggcccucg agaacaagaa gaagcagcua ucggcgggag gcaagaaccu      480
cagcaaggag gaagagagg aacucaggag guugaccgag gaagacgaga gaagggaaag       540
aagaguagcc ggcccgccgg uuggggugu gaaccccuc gaagguggau cgaggggagc        600 gcccggggc ggcuucgucc ccaaucugga gggagucccg gagucccccu ucucucggac       660
cggggagggg cuggacauca ggggaaacca gggauuucca uaggauauac ucuucccagc      720
cgauccgccc uuuucucccc agaguugucg accccaguga auaaagcggg uuccacuca       780 cagguuugcg ucucgcgucc uucuuuccuc uuc                                   813

<210> SEQ ID NO 44
<211> LENGTH: 57
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 44
ggguccaccu ccucgcgguc cgaccugggc augcggcuuc gcauggcuaa gggaccc         57

<210> SEQ ID NO 45
<211> LENGTH: 57
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 45
ggguccaccu ccucgcgguc ccagcugggc augcggcuuc gcauggcuaa gggaccc         57

<210> SEQ ID NO 46
<211> LENGTH: 57
<212> TYPE: RNA
<213> ORGANISM: Artificial Sequence
<220> FEATURE:
<223> OTHER INFORMATION: Description of Artificial Sequence:  synthetic
      RNA sequence
```

```
<400> SEQUENCE: 46
ggguccaccu ccucgcgguc cgaccugggc augccuucgg gcauggcuaa gggaccc        57

<210> SEQ ID NO 47
<211> LENGTH: 57
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 47
ggguccaccu ccucgcgguc cgcccugggc augcggcuuc gcauggcuaa gggaccc        57

<210> SEQ ID NO 48
<211> LENGTH: 57
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 48
ggguccaccu ccucgcgguc cggccugggc augcggcuuc gcauggcuaa gggaccc        57

<210> SEQ ID NO 49
<211> LENGTH: 57
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 49
ggguccaccu ccucgcgguc cguccugggc augcggcuuc gcauggcuaa gggaccc        57

<210> SEQ ID NO 50
<211> LENGTH: 57
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 50
ggguccaccu ccucgcgguc cgaacugggc augcggcuuc gcauggcuaa gggaccc        57

<210> SEQ ID NO 51
<211> LENGTH: 57
<212> TYPE: RNA
<213> ORGANISM: Artificial Sequence
<220> FEATURE:
<223> OTHER INFORMATION: Description of Artificial Sequence: synthetic
      RNA sequence

<400> SEQUENCE: 51
ggguccaccu ccucgcgguc cgagcugggc augcggcuuc gcauggcuaa gggaccc        57

<210> SEQ ID NO 52
<211> LENGTH: 57
<212> TYPE: RNA
<213> ORGANISM: Artificial Sequence
<220> FEATURE:
<223> OTHER INFORMATION: Description of Artificial Sequence: synthetic
      RNA sequence
```

-continued

```
<400> SEQUENCE: 52
ggguccaccu ccucgcgguc cgaucugggc augcggcuuc gcauggcuaa gggaccc      57

<210> SEQ ID NO 53
<211> LENGTH: 37
<212> TYPE: RNA
<213> ORGANISM: Artificial Sequence
<220> FEATURE:
<223> OTHER INFORMATION: Description of Artificial Sequence:  synthetic
      RNA sequence

<400> SEQUENCE: 53
ggguccaccu ccucgcgguc cgaccugggc augcgcc                             37

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence:  synthetic
      sequence which is comprised of ribonucleotides or
      a combination of both ribonucleotides and
      deoxyribonucleotides

<400> SEQUENCE: 54
ggcauggcua agggaccc                                                  18

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: RNA/DNA
      sequence

<400> SEQUENCE: 55
ggcgcauggc uaagggaccc                                                20

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: RT primer

<400> SEQUENCE: 56
ctttgatgtt ccccagccag g                                              21

<210> SEQ ID NO 57
<211> LENGTH: 10
<212> TYPE: RNA
<213> ORGANISM: Artificial Sequence
<220> FEATURE:
<223> OTHER INFORMATION: Description of Artificial Sequence: Synthetic
      RNA sequence

<400> SEQUENCE: 57
caguggugg                                                            10

<210> SEQ ID NO 58
<211> LENGTH: 20
<212> TYPE: RNA
<213> ORGANISM: Artificial Sequence
<220> FEATURE:
<223> OTHER INFORMATION: Description of Artificial Sequence: Synthetic
      RNA sequence
```

```
<400> SEQUENCE: 58
ggcgcauggc uaagggaccc                                                    20

<210> SEQ ID NO 59
<211> LENGTH: 57
<212> TYPE: RNA
<213> ORGANISM: Artificial Sequence
<220> FEATURE:
<223> OTHER INFORMATION: Description of Artificial Sequence: Synthetic
      RNA sequence

<400> SEQUENCE: 59
ggguccaccu ccucgcggug ggauaugggc augcggcuuc gcauggcuaa gggaccc           57

<210> SEQ ID NO 60
<211> LENGTH: 11
<212> TYPE: RNA
<213> ORGANISM: Artificial Sequence
<220> FEATURE:
<223> OTHER INFORMATION: Description of Artificial Sequence: Synthetic
      RNA sequence

<400> SEQUENCE: 60
gggcggcugg g                                                             11

<210> SEQ ID NO 61
<211> LENGTH: 57
<212> TYPE: DNA
<213> ORGANISM: Artificial Sequence
<220> FEATURE:
<223> OTHER INFORMATION: Description of Artificial Sequence: Synthetic
      nucleotide sequence comprised of ribonucleotides or a
      combination of ribonucleotides and
      deoxyribonucleotides
<220> FEATURE:
<221> NAME/KEY: misc_feature
<222> LOCATION: (20)..(25)
<223> OTHER INFORMATION: n is a or g or c or t/u

<400> SEQUENCE: 61
ggguccaccu ccucgcggun nnnnnugggc augcggcuuc gcauggcuaa gggaccc           57

<210> SEQ ID NO 62
<211> LENGTH: 57
<212> TYPE: DNA
<213> ORGANISM: Artificial Sequence
<220> FEATURE:
<223> OTHER INFORMATION: Description of Artificial Sequence: nucleotide
      sequence comprised of ribonucleotides or a
      combination of ribonucleotides and
      deoxyribonucleotides
<220> FEATURE:
<221> NAME/KEY: misc_feature
<222> LOCATION: (20)..(25)
<223> OTHER INFORMATION: n is a or g or c or t/u

<400> SEQUENCE: 62
ggguccaccu ccucgcggun nnnnnugggc augccuucgg gcauggcuaa gggaccc           57

<210> SEQ ID NO 63
<211> LENGTH: 37
<212> TYPE: DNA
<213> ORGANISM: Artificial Sequence
<220> FEATURE:
<223> OTHER INFORMATION: Description of Artificial Sequence: nucleotide
      sequence comprised of ribonucleotides or a
      combination of ribonucleotides and
      deoxyribonucleotides
<220> FEATURE:
```

```
<221> NAME/KEY: misc_feature
<222> LOCATION: (20)..(25)
<223> OTHER INFORMATION: n is a or g or c or t/u

<400> SEQUENCE: 63 gguccaccu ccucgcggun nnnnnugggc augcgcc                          37

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: nucleotide
      sequence comprised of ribonucleotides or a
      combination of ribonucleotides and
      deoxyribonucleotides

<400> SEQUENCE: 64
ggcgcauggc uaagggaccc                                            20

<210> SEQ ID NO 65
<211> LENGTH: 37
<212> TYPE: DNA
<213> ORGANISM: Artificial Sequence
<220> FEATURE:
<223> OTHER INFORMATION: Description of Artificial Sequence: Synthetic
      nucleotide sequence comprised of ribonucleotides or a combination
      of ribonucleotides and deoxyribonucleotides
<220> FEATURE:
<221> NAME/KEY: misc_feature
<222> LOCATION: (20)..(25)
<223> OTHER INFORMATION: n is a or c or g or t/u
<220> FEATURE:
<221> NAME/KEY: misc_feature
<222> LOCATION: (35)..(35)
<223> OTHER INFORMATION: s is g or c
<220> FEATURE:
<221> NAME/KEY: misc_feature
<222> LOCATION: (36)..(36)
<223> OTHER INFORMATION: b is g or c or t/u
<220> FEATURE:
<221> NAME/KEY: misc_feature
<222> LOCATION: (37)..(37)
<223> OTHER INFORMATION: y is c or t/u

<400> SEQUENCE: 65
ggguccaccu ccucgcggun nnnnnugggc augcsby                         37

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide sequence comprised of ribonucleotides or a combination
      of ribonucleotides and deoxyribonucleotides
<220> FEATURE:
<221> NAME/KEY: misc_feature
<222> LOCATION: (1)..(1)
<223> OTHER INFORMATION: b is g or c or t/u
<220> FEATURE:
<221> NAME/KEY: misc_feature
<222> LOCATION: (2)..(2)
<223> OTHER INFORMATION: k is g or t/u
<220> FEATURE:
<221> NAME/KEY: misc_feature
<222> LOCATION: (3)..(3)
<223> OTHER INFORMATION: s is g or c

<400> SEQUENCE: 66
bksgcauggc uaagggaccc                                            20
```